(12) United States Patent
Blain

(10) Patent No.: US 9,931,142 B2
(45) Date of Patent: Apr. 3, 2018

(54) IMPLANT AND METHOD FOR FACET IMMOBILIZATION

(71) Applicant: Spinal Elements, Inc., Carlsbad, CA (US)

(72) Inventor: Jason Blain, Encinitas, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 3 days.

(21) Appl. No.: 15/360,400

(22) Filed: Nov. 23, 2016

(65) Prior Publication Data
US 2017/0128109 A1 May 11, 2017
US 2017/0340364 A9 Nov. 30, 2017

Related U.S. Application Data

(60) Division of application No. 12/106,248, filed on Apr. 18, 2008, now Pat. No. 9,504,583, which is a continuation-in-part of application No. 10/865,073, filed on Jun. 10, 2004, now Pat. No. 7,846,183.

(51) Int. Cl.
*A61B 17/70* (2006.01)
*A61F 2/44* (2006.01)
*A61F 2/30* (2006.01)

(52) U.S. Cl.
CPC ........ *A61B 17/7064* (2013.01); *A61F 2/4405* (2013.01); *A61F 2002/302* (2013.01); *A61F 2002/30512* (2013.01); *A61F 2002/30754* (2013.01); *A61F 2002/30968* (2013.01)

(58) Field of Classification Search
CPC ............ A61B 17/7056; A61B 17/7062; A61B 17/7064; A61B 17/7067; A61B 17/707; A61B 17/7071; A61F 2/4405
See application file for complete search history.

(56) References Cited

U.S. PATENT DOCUMENTS

| 86,016 A | 1/1869 | Howell |
| 1,630,239 A | 5/1927 | Binkley et al. |
| 1,822,280 A | 9/1931 | Ervay |
| 1,822,330 A | 9/1931 | Anslie |
| 2,486,303 A | 10/1949 | Longfellow |
| 2,706,023 A | 4/1955 | Merritt |
| 3,111,945 A | 11/1963 | Von Solbrig |
| 3,149,808 A | 9/1964 | Weckesser |

(Continued)

FOREIGN PATENT DOCUMENTS

| CA | 2 437 575 | 4/2009 |
| DE | 93 04 368 | 5/1993 |

(Continued)

OTHER PUBLICATIONS

Translation of DE 10135771 A1.*

(Continued)

*Primary Examiner* — Lynnsy Summitt

(57) ABSTRACT

Devices and methods are provided for immobilizing facet joints of the vertebral column. Embodiments of the invention provide an implant that is inserted in a facet joint from which cartilage has been removed, and which retains the approximate original spacing of the facets in the joint. A retaining arrangement, such as an adhesive, a threaded fastener, or a screw is then used to secure the implant in the joint.

19 Claims, 11 Drawing Sheets

(56) References Cited

U.S. PATENT DOCUMENTS

| | | |
|---|---|---|
| 3,570,497 A | 3/1971 | Lemole |
| 3,867,728 A | 2/1975 | Stubstad et al. |
| 3,875,595 A | 4/1975 | Froning |
| 3,879,767 A | 4/1975 | Stubstad |
| 4,001,896 A | 1/1977 | Arkangel |
| 4,037,603 A | 7/1977 | Wendorff |
| 4,085,466 A | 4/1978 | Goodfellow et al. |
| 4,119,091 A | 10/1978 | Partridge |
| 4,156,296 A | 5/1979 | Johnson et al. |
| 4,231,121 A | 11/1980 | Lewis |
| D261,935 S | 11/1981 | Halloran |
| 4,312,337 A | 1/1982 | Donohue |
| 4,323,217 A | 4/1982 | Dochterman |
| 4,349,921 A | 9/1982 | Kuntz |
| 4,502,161 A | 3/1985 | Wall |
| D279,502 S | 7/1985 | Halloran |
| D279,503 S | 7/1985 | Halloran |
| 4,535,764 A | 8/1985 | Ebert |
| 4,573,458 A | 3/1986 | Lower |
| 4,573,459 A | 3/1986 | Litton |
| 4,634,445 A | 1/1987 | Helal |
| 4,662,371 A | 5/1987 | Whipple et al. |
| 4,706,659 A | 11/1987 | Matthews et al. |
| 4,714,469 A | 12/1987 | Kenna |
| 4,722,331 A | 2/1988 | Fox |
| 4,730,615 A | 3/1988 | Sutherland et al. |
| 4,759,766 A | 7/1988 | Buettner-Janz et al. |
| 4,759,769 A | 7/1988 | Hedman et al. |
| 4,772,287 A | 9/1988 | Ray et al. |
| 4,773,402 A | 9/1988 | Asher et al. |
| 4,834,757 A | 5/1989 | Brantigan |
| 4,863,477 A | 9/1989 | Monson |
| 4,904,260 A | 2/1990 | Ray et al. |
| 4,907,577 A | 3/1990 | Wu |
| 4,911,718 A | 3/1990 | Lee et al. |
| 4,919,667 A | 4/1990 | Richmond |
| 4,923,471 A | 5/1990 | Morgan |
| 4,936,848 A | 6/1990 | Bagby |
| 4,941,466 A | 7/1990 | Romano |
| 4,959,065 A | 9/1990 | Arnett et al. |
| 4,969,909 A | 11/1990 | Barouk |
| 5,000,165 A | 3/1991 | Watanabe |
| 5,002,546 A | 3/1991 | Romano |
| 5,011,484 A | 4/1991 | Bréard |
| 5,015,255 A | 5/1991 | Kuslich |
| 5,047,055 A | 9/1991 | Bao et al. |
| 5,062,845 A | 11/1991 | Kuslich |
| 5,071,437 A | 12/1991 | Steffee |
| 5,092,866 A | 3/1992 | Breard et al. |
| 5,112,013 A | 5/1992 | Tolbert et al. |
| 5,112,346 A | 5/1992 | Hiltebrandt et al. |
| 5,127,912 A | 7/1992 | Ray et al. |
| 5,135,188 A | 8/1992 | Anderson et al. |
| 5,147,404 A | 9/1992 | Downey |
| 5,171,280 A | 12/1992 | Baumgartner |
| 5,192,326 A | 3/1993 | Bao et al. |
| 5,209,755 A | 5/1993 | Abrahan et al. |
| 5,258,031 A | 11/1993 | Salib et al. |
| 5,282,861 A | 2/1994 | Kaplan |
| 5,286,249 A | 2/1994 | Thibodaux |
| 5,300,073 A | 4/1994 | Ray et al. |
| 5,306,275 A | 4/1994 | Bryan |
| 5,306,308 A | 4/1994 | Gross et al. |
| 5,306,309 A | 4/1994 | Wagner et al. |
| 5,330,479 A | 7/1994 | Whitmore |
| 5,360,431 A | 11/1994 | Puna et al. |
| 5,368,596 A | 11/1994 | Burkhart |
| 5,370,697 A | 12/1994 | Baumgartner |
| 5,372,598 A | 12/1994 | Luhr et al. |
| 5,400,784 A | 3/1995 | Durand et al. |
| 5,401,269 A | 3/1995 | Buttner-Janz et al. |
| 5,413,576 A | 5/1995 | Rivard |
| 5,415,661 A | 5/1995 | Holmes |
| 5,425,773 A | 6/1995 | Boyd et al. |
| 5,437,672 A | 8/1995 | Alleyne |
| 5,445,639 A | 8/1995 | Kuslich et al. |
| 5,458,642 A | 10/1995 | Beer et al. |
| 5,458,643 A | 10/1995 | Oka et al. |
| 5,462,542 A | 10/1995 | Alesi, Jr. |
| 5,487,756 A | 1/1996 | Kallesoe et al. |
| 5,491,882 A | 2/1996 | Walston et al. |
| 5,496,318 A | 3/1996 | Howland et al. |
| 5,507,823 A | 4/1996 | Walston et al. |
| 5,509,918 A | 4/1996 | Romano |
| 5,514,180 A | 5/1996 | Heggeness et al. |
| 5,527,312 A | 6/1996 | Ray |
| 5,527,314 A | 6/1996 | Brumfield et al. |
| 5,534,028 A | 7/1996 | Bao et al. |
| 5,534,030 A | 7/1996 | Navarro et al. |
| 5,540,706 A | 7/1996 | Aust et al. |
| 5,545,229 A | 8/1996 | Parsons et al. |
| 5,549,619 A | 8/1996 | Peters et al. |
| 5,556,431 A | 9/1996 | Buttner-Janz |
| 5,562,738 A | 10/1996 | Boyd et al. |
| 5,571,105 A | 11/1996 | Gundolf |
| 5,571,131 A | 11/1996 | Ek et al. |
| 5,571,189 A | 11/1996 | Kuslich |
| 5,571,191 A | 11/1996 | Fitz |
| 5,577,995 A | 11/1996 | Walker et al. |
| 5,586,989 A | 12/1996 | Bray, Jr. |
| 5,591,165 A | 1/1997 | Jackson |
| 5,603,713 A | 2/1997 | Aust et al. |
| 5,638,700 A | 6/1997 | Shechter |
| 5,645,597 A | 7/1997 | Krapiva |
| 5,645,599 A | 7/1997 | Samani |
| 5,649,947 A | 7/1997 | Auerbach et al. |
| 5,653,762 A | 8/1997 | Pisharodi |
| 5,674,295 A | 10/1997 | Ray et al. |
| 5,674,296 A | 10/1997 | Bryan et al. |
| 5,676,701 A | 10/1997 | Yuan et al. |
| 5,683,464 A | 11/1997 | Wagner et al. |
| 5,683,466 A | 11/1997 | Vitale |
| 5,700,265 A | 12/1997 | Romano |
| 5,702,450 A | 12/1997 | Bisserie |
| 5,707,373 A | 1/1998 | Sevrain et al. |
| 5,713,542 A | 2/1998 | Benoit |
| 5,716,415 A | 2/1998 | Steffee |
| 5,725,582 A | 3/1998 | Bevan et al. |
| 5,741,260 A | 4/1998 | Songer et al. |
| 5,741,261 A | 4/1998 | Moskovitz et al. |
| D395,138 S | 6/1998 | Ohata |
| 5,766,251 A | 6/1998 | Koshino |
| 5,766,253 A | 6/1998 | Brosnahan |
| 5,772,663 A | 6/1998 | Whiteside et al. |
| 5,797,916 A | 8/1998 | McDowell |
| 5,824,093 A | 10/1998 | Ray et al. |
| 5,824,094 A | 10/1998 | Serhan et al. |
| 5,836,948 A | 11/1998 | Zucherman et al. |
| 5,851,208 A | 12/1998 | Trott |
| 5,860,977 A | 1/1999 | Zucherman et al. |
| 5,865,846 A | 2/1999 | Bryan et al. |
| 5,868,745 A | 2/1999 | Alleyne |
| 5,876,404 A | 3/1999 | Zucherman et al. |
| 5,879,396 A | 3/1999 | Walston et al. |
| 5,888,203 A | 3/1999 | Goldberg |
| 5,893,889 A | 4/1999 | Harrington |
| 5,895,428 A | 4/1999 | Berry |
| RE36,221 E | 6/1999 | Breard et al. |
| 5,918,604 A | 7/1999 | Whelan |
| 5,951,555 A | 9/1999 | Rehak et al. |
| 5,964,765 A | 10/1999 | Fenton et al. |
| 5,993,452 A | 11/1999 | Vandewalle |
| 5,997,542 A | 12/1999 | Burke |
| 6,001,130 A | 12/1999 | Bryan et al. |
| 6,014,588 A | 1/2000 | Fitz |
| 6,019,763 A | 2/2000 | Nakamura et al. |
| 6,019,792 A | 2/2000 | Cauthen |
| 6,039,763 A | 3/2000 | Shelokov |
| 6,048,342 A | 4/2000 | Zucherman et al. |
| 6,050,998 A | 4/2000 | Fletcher |
| 6,063,121 A | 5/2000 | Xavier et al. |
| 6,066,325 A | 5/2000 | Wallace et al. |
| 6,068,630 A | 5/2000 | Zucherman et al. |
| RE36,758 E | 6/2000 | Fitz |

(56) References Cited

U.S. PATENT DOCUMENTS

| | | |
|---|---|---|
| 6,080,157 A | 6/2000 | Cathro et al. |
| 6,099,531 A | 8/2000 | Bonutti |
| 6,102,347 A | 8/2000 | Benoit |
| 6,106,558 A | 8/2000 | Picha |
| 6,113,637 A | 9/2000 | Gi, II et al. |
| 6,132,464 A | 10/2000 | Martin |
| 6,132,465 A | 10/2000 | Ray et al. |
| 6,146,422 A | 11/2000 | Lawson |
| 6,156,067 A | 12/2000 | Bryan et al. |
| 6,179,839 B1 | 1/2001 | Weiss et al. |
| D439,340 S | 3/2001 | Michelson |
| 6,200,322 B1 | 3/2001 | Branch et al. |
| 6,293,949 B1 | 9/2001 | Justis et al. |
| D450,122 S | 11/2001 | Michelson |
| 6,325,803 B1 | 12/2001 | Schumacher et al. |
| D454,953 S | 3/2002 | Michelson |
| 6,368,325 B1 | 4/2002 | McKinley et al. |
| 6,368,350 B1 | 4/2002 | Erickson et al. |
| 6,371,958 B1 | 4/2002 | Overaker |
| 6,375,573 B2 | 4/2002 | Romano |
| 6,379,386 B1 | 4/2002 | Resch et al. |
| D460,188 S | 7/2002 | Michelson |
| D460,189 S | 7/2002 | Michelson |
| 6,419,678 B1 | 7/2002 | Asfora |
| 6,419,703 B1 | 7/2002 | Fallin et al. |
| 6,436,099 B1 | 8/2002 | Drewry et al. |
| 6,436,101 B1 | 8/2002 | Hamada et al. |
| 6,436,146 B1 | 8/2002 | Hassler et al. |
| D463,560 S | 9/2002 | Michelson |
| 6,470,207 B1 | 10/2002 | Simon et al. |
| 6,547,795 B2 * | 4/2003 | Schneiderman ...... A61B 17/864 606/102 |
| 6,565,605 B2 | 5/2003 | Goble et al. |
| 6,572,617 B1 | 6/2003 | Senegas |
| 6,579,318 B2 | 6/2003 | Varga et al. |
| 6,579,319 B2 | 6/2003 | Goble et al. |
| 6,589,244 B1 | 7/2003 | Sevrain et al. |
| 6,600,956 B2 | 7/2003 | Maschino et al. |
| 6,607,530 B1 | 8/2003 | Carl et al. |
| 6,610,091 B1 | 8/2003 | Reiley |
| D479,331 S | 9/2003 | Pike et al. |
| 6,626,944 B1 | 9/2003 | Taylor |
| 6,641,614 B1 | 11/2003 | Wagner et al. |
| 6,656,195 B2 | 12/2003 | Peters et al. |
| 6,669,697 B1 | 12/2003 | Pisharodi |
| 6,669,698 B1 * | 12/2003 | Tromanhauser ... A61B 17/1615 606/104 |
| 6,669,729 B2 | 12/2003 | Chin |
| 6,706,068 B2 | 3/2004 | Ferree |
| 6,743,232 B2 | 6/2004 | Overaker et al. |
| 6,761,720 B1 | 7/2004 | Senegas |
| 6,764,491 B2 | 7/2004 | Frey et al. |
| 6,770,095 B2 | 8/2004 | Grinberg et al. |
| 6,783,527 B2 | 8/2004 | Drewry et al. |
| 6,790,210 B1 | 9/2004 | Cragg et al. |
| 6,802,863 B2 | 10/2004 | Lawson et al. |
| 6,811,567 B2 | 11/2004 | Reiley |
| 6,902,566 B2 | 6/2005 | Zucherman et al. |
| 6,908,484 B2 | 6/2005 | Zubok et al. |
| 6,966,930 B2 | 11/2005 | Arnin et al. |
| 6,974,478 B2 | 12/2005 | Reiley et al. |
| 6,974,479 B2 | 12/2005 | Trieu |
| D517,404 S | 3/2006 | Schluter |
| 7,008,429 B2 | 3/2006 | Golobek |
| 7,013,675 B2 | 3/2006 | Marquez-Pickering |
| 7,051,451 B2 | 5/2006 | Augostino et al. |
| 7,074,238 B2 | 7/2006 | Stinson et al. |
| 7,101,375 B2 | 9/2006 | Zucherman et al. |
| 7,223,269 B2 | 5/2007 | Chappuis |
| D565,180 S | 3/2008 | Liao |
| 7,371,238 B2 | 5/2008 | Sololeski et al. |
| 7,458,981 B2 | 12/2008 | Fielding et al. |
| 7,517,358 B2 | 4/2009 | Petersen |
| 7,537,611 B2 | 5/2009 | Lee |
| 7,559,940 B2 | 7/2009 | McGuire et al. |
| 7,563,286 B2 | 7/2009 | Gerber et al. |
| 7,585,300 B2 | 9/2009 | Cha |
| 7,608,094 B2 * | 10/2009 | Falahee ............... A61B 17/1757 606/247 |
| 7,608,104 B2 | 10/2009 | Yuan et al. |
| 7,695,472 B2 | 4/2010 | Young |
| 7,799,053 B2 * | 9/2010 | Haid, Jr. ............. A61B 17/7064 606/246 |
| 7,799,077 B2 | 9/2010 | Lang et al. |
| 7,806,895 B2 | 10/2010 | Weier et al. |
| 7,846,183 B2 | 12/2010 | Blain |
| 7,862,590 B2 | 1/2011 | Lim et al. |
| 7,935,136 B2 | 5/2011 | Alamin et al. |
| D643,121 S | 8/2011 | Milford et al. |
| 7,993,370 B2 | 8/2011 | Jahng |
| 7,998,172 B2 | 8/2011 | Blain |
| 8,052,728 B2 | 11/2011 | Hestad |
| 8,109,971 B2 | 2/2012 | Hale |
| 8,133,225 B2 | 3/2012 | Pieske |
| 8,163,016 B2 | 4/2012 | Linares |
| 8,192,468 B2 | 6/2012 | Biedermann et al. |
| 8,216,275 B2 | 7/2012 | Fielding et al. |
| 8,246,655 B2 | 8/2012 | Jackson et al. |
| 8,292,954 B2 | 10/2012 | Robinson et al. |
| 8,306,307 B2 | 11/2012 | Koike et al. |
| 8,394,125 B2 | 3/2013 | Assell |
| 8,460,346 B2 | 6/2013 | Ralph et al. |
| 8,486,078 B2 | 7/2013 | Carl et al. |
| 8,496,691 B2 | 7/2013 | Blain |
| 8,579,903 B2 | 11/2013 | Carl |
| 8,652,137 B2 | 2/2014 | Blain et al. |
| 8,740,942 B2 | 6/2014 | Blain |
| 8,740,949 B2 | 6/2014 | Blain |
| 8,784,423 B2 | 7/2014 | Kowarsch et al. |
| 8,858,597 B2 | 10/2014 | Blain |
| 8,882,804 B2 | 11/2014 | Blain |
| 8,961,613 B2 | 2/2015 | Assell et al. |
| D724,733 S | 3/2015 | Blain et al. |
| 8,974,456 B2 | 3/2015 | Allen et al. |
| 8,979,529 B2 | 3/2015 | Marcus |
| 8,992,533 B2 | 3/2015 | Blain et al. |
| 8,998,953 B2 | 4/2015 | Blain |
| 9,017,389 B2 | 4/2015 | Assell et al. |
| 9,060,787 B2 | 6/2015 | Blain et al. |
| D739,935 S | 9/2015 | Blain et al. |
| 9,149,283 B2 | 10/2015 | Assell et al. |
| 9,161,763 B2 | 10/2015 | Assell et al. |
| 9,179,943 B2 | 11/2015 | Blain |
| 9,220,547 B2 | 12/2015 | Blain et al. |
| D748,262 S | 1/2016 | Blain |
| 9,233,006 B2 | 1/2016 | Assell et al. |
| D748,793 S | 2/2016 | Blain |
| 9,265,546 B2 | 2/2016 | Blain |
| 9,271,765 B2 | 3/2016 | Blain |
| 9,301,786 B2 | 4/2016 | Blain |
| 9,314,277 B2 | 4/2016 | Assell et al. |
| 9,345,488 B2 | 5/2016 | Assell et al. |
| 9,421,044 B2 | 8/2016 | Blain et al. |
| D765,853 S | 9/2016 | Blain et al. |
| D765,854 S | 9/2016 | Blain et al. |
| 9,456,855 B2 | 10/2016 | Blain et al. |
| 9,517,077 B2 | 12/2016 | Blain et al. |
| D777,921 S | 1/2017 | Blain et al. |
| D780,315 S | 2/2017 | Blain et al. |
| 9,572,602 B2 | 2/2017 | Blain et al. |
| 2001/0018614 A1 | 8/2001 | Bianchi |
| 2002/0018799 A1 | 2/2002 | Spector et al. |
| 2002/0019637 A1 | 2/2002 | Frey et al. |
| 2002/0029039 A1 | 3/2002 | Zucherman et al. |
| 2002/0040227 A1 | 4/2002 | Harari |
| 2002/0065557 A1 | 5/2002 | Goble et al. |
| 2002/0072800 A1 | 6/2002 | Goble et al. |
| 2002/0077700 A1 | 6/2002 | Varga et al. |
| 2002/0086047 A1 | 7/2002 | Mueller et al. |
| 2002/0120335 A1 | 8/2002 | Angelucci et al. |
| 2002/0123806 A1 | 9/2002 | Reiley |
| 2002/0151895 A1 | 10/2002 | Soboleski et al. |
| 2002/0173800 A1 | 11/2002 | Dreyfuss et al. |
| 2002/0173813 A1 | 11/2002 | Peterson et al. |

(56) References Cited

U.S. PATENT DOCUMENTS

| | | |
|---|---|---|
| 2002/0198527 A1 | 12/2002 | Muckter |
| 2003/0004572 A1 | 1/2003 | Goble et al. |
| 2003/0028250 A1 | 2/2003 | Reiley et al. |
| 2003/0040797 A1 | 2/2003 | Fallin et al. |
| 2003/0120343 A1 | 6/2003 | Whelan |
| 2003/0176919 A1 | 9/2003 | Schmieding |
| 2003/0176922 A1 | 9/2003 | Lawson et al. |
| 2003/0187454 A1 | 10/2003 | Gill et al. |
| 2003/0191532 A1 | 10/2003 | Goble et al. |
| 2003/0204259 A1 | 10/2003 | Goble et al. |
| 2003/0216669 A1 | 11/2003 | Lang et al. |
| 2003/0233146 A1 | 12/2003 | Grinberg et al. |
| 2004/0006391 A1 | 1/2004 | Reiley |
| 2004/0010318 A1 | 1/2004 | Ferree |
| 2004/0024462 A1 | 2/2004 | Ferree et al. |
| 2004/0049271 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0059429 A1 | 3/2004 | Amin et al. |
| 2004/0087954 A1 | 5/2004 | Allen et al. |
| 2004/0111093 A1* | 6/2004 | Chappuis ............ A61B 17/1671 606/86 R |
| 2004/0116927 A1 | 6/2004 | Graf |
| 2004/0127989 A1 | 7/2004 | Dooris et al. |
| 2004/0143264 A1 | 7/2004 | McAfee |
| 2004/0176844 A1 | 9/2004 | Zubok et al. |
| 2004/0199166 A1 | 10/2004 | Schmieding et al. |
| 2004/0215341 A1 | 10/2004 | Sybert et al. |
| 2004/0230201 A1 | 11/2004 | Yuan et al. |
| 2004/0230304 A1 | 11/2004 | Yuan et al. |
| 2005/0010291 A1 | 1/2005 | Stinson et al. |
| 2005/0015146 A1 | 1/2005 | Louis et al. |
| 2005/0043797 A1 | 2/2005 | Lee |
| 2005/0043799 A1 | 2/2005 | Reiley |
| 2005/0049705 A1 | 3/2005 | Hale et al. |
| 2005/0055096 A1 | 3/2005 | Serhan et al. |
| 2005/0059972 A1 | 3/2005 | Biscup |
| 2005/0131409 A1 | 6/2005 | Chervitz et al. |
| 2005/0131538 A1 | 6/2005 | Chervitz et al. |
| 2005/0143818 A1 | 6/2005 | Yuan et al. |
| 2005/0159746 A1 | 7/2005 | Grab et al. |
| 2005/0197700 A1 | 9/2005 | Boehem et al. |
| 2005/0216017 A1 | 9/2005 | Fielding et al. |
| 2005/0240201 A1 | 10/2005 | Yeung |
| 2005/0251256 A1 | 11/2005 | Reiley |
| 2005/0256494 A1 | 11/2005 | Datta |
| 2006/0004367 A1 | 1/2006 | Alamin et al. |
| 2006/0036323 A1 | 2/2006 | Carl et al. |
| 2006/0041311 A1 | 2/2006 | McLeer |
| 2006/0084985 A1 | 4/2006 | Kim |
| 2006/0085006 A1 | 4/2006 | Ek et al. |
| 2006/0085072 A1 | 4/2006 | Funk et al. |
| 2006/0111782 A1 | 5/2006 | Petersen |
| 2006/0116684 A1 | 6/2006 | Whelan |
| 2006/0149375 A1 | 7/2006 | Yuan et al. |
| 2006/0200137 A1 | 9/2006 | Soboleski et al. |
| 2006/0241601 A1 | 10/2006 | Trautwein et al. |
| 2006/0241758 A1 | 10/2006 | Peterman et al. |
| 2006/0293691 A1 | 12/2006 | Mitra et al. |
| 2007/0055236 A1 | 3/2007 | Hudgins et al. |
| 2007/0055252 A1 | 3/2007 | Blain et al. |
| 2007/0078464 A1 | 4/2007 | Jones et al. |
| 2007/0118218 A1 | 5/2007 | Hooper |
| 2007/0149976 A1 | 6/2007 | Hale et al. |
| 2007/0179619 A1 | 8/2007 | Grab |
| 2007/0250166 A1 | 10/2007 | McKay |
| 2007/0270812 A1 | 11/2007 | Peckham |
| 2008/0009866 A1 | 1/2008 | Alamin et al. |
| 2008/0058929 A1 | 3/2008 | Whelan |
| 2008/0177264 A1 | 7/2008 | Alamin et al. |
| 2008/0183211 A1 | 7/2008 | Lamborne et al. |
| 2008/0228225 A1 | 9/2008 | Trautwein et al. |
| 2008/0287996 A1 | 11/2008 | Soholeski et al. |
| 2009/0005818 A1 | 1/2009 | Chin et al. |
| 2009/0005873 A1 | 1/2009 | Slivka et al. |
| 2009/0018662 A1 | 1/2009 | Pasquet et al. |
| 2009/0024166 A1 | 1/2009 | Carl et al. |
| 2009/0076617 A1 | 3/2009 | Ralph et al. |
| 2009/0125066 A1 | 5/2009 | Kraus et al. |
| 2009/0138048 A1 | 5/2009 | Baccelli et al. |
| 2009/0171360 A1 | 7/2009 | Whelan |
| 2009/0198282 A1 | 8/2009 | Fielding et al. |
| 2009/0264928 A1 | 10/2009 | Blain |
| 2009/0264929 A1 | 10/2009 | Alamin et al. |
| 2009/0270918 A1 | 10/2009 | Attia et al. |
| 2009/0270929 A1 | 10/2009 | Suddaby |
| 2009/0326589 A1 | 12/2009 | Lemoine et al. |
| 2010/0010548 A1 | 1/2010 | Hermida Ochoa |
| 2010/0076503 A1 | 3/2010 | Beyar et al. |
| 2010/0131008 A1 | 5/2010 | Overes et al. |
| 2010/0179553 A1 | 7/2010 | Ralph et al. |
| 2010/0185241 A1 | 7/2010 | Malandain et al. |
| 2010/0191286 A1 | 7/2010 | Butler |
| 2010/0204700 A1 | 8/2010 | Falahee |
| 2010/0204732 A1 | 8/2010 | Aschmann et al. |
| 2010/0234894 A1 | 9/2010 | Alamin et al. |
| 2010/0274289 A1 | 10/2010 | Carls et al. |
| 2010/0298829 A1 | 11/2010 | Schaller et al. |
| 2010/0318133 A1 | 12/2010 | Tornier |
| 2011/0022089 A1 | 1/2011 | Assell et al. |
| 2011/0040301 A1 | 2/2011 | Blain et al. |
| 2011/0082503 A1 | 4/2011 | Blain |
| 2011/0098816 A1 | 4/2011 | Jacob et al. |
| 2011/0160772 A1 | 6/2011 | Arcenio et al. |
| 2011/0172712 A1 | 7/2011 | Chee et al. |
| 2011/0295318 A1 | 12/2011 | Alamin et al. |
| 2011/0313456 A1 | 12/2011 | Blain |
| 2012/0035658 A1 | 2/2012 | Goble et al. |
| 2012/0046749 A1 | 2/2012 | Tatsumi |
| 2012/0101502 A1 | 4/2012 | Kartalian et al. |
| 2012/0150231 A1 | 6/2012 | Alamin et al. |
| 2012/0221048 A1 | 8/2012 | Blain |
| 2012/0221049 A1 | 8/2012 | Blain |
| 2012/0221060 A1 | 8/2012 | Blain |
| 2012/0245586 A1 | 9/2012 | Lehenkari et al. |
| 2012/0271354 A1 | 10/2012 | Baccelli et al. |
| 2012/0277801 A1 | 11/2012 | Marik et al. |
| 2012/0310244 A1 | 12/2012 | Blain et al. |
| 2013/0023878 A1 | 1/2013 | Belliard et al. |
| 2013/0041410 A1 | 2/2013 | Hestad et al. |
| 2013/0079778 A1 | 3/2013 | Azuero et al. |
| 2013/0123923 A1 | 5/2013 | Pavlov et al. |
| 2013/0245693 A1 | 9/2013 | Blain |
| 2013/0325065 A1 | 12/2013 | Malandain et al. |
| 2014/0012318 A1 | 1/2014 | Goel |
| 2014/0066758 A1 | 3/2014 | Marik et al. |
| 2014/0228883 A1 | 8/2014 | Blain |
| 2014/0257397 A1 | 9/2014 | Akbarnia et al. |
| 2014/0277142 A1 | 9/2014 | Blain |
| 2014/0277148 A1 | 9/2014 | Blain et al. |
| 2014/0277149 A1 | 9/2014 | Rooney et al. |
| 2014/0336653 A1 | 11/2014 | Bromer |
| 2014/0378976 A1 | 12/2014 | Garcia |
| 2015/0081023 A1 | 3/2015 | Blain |
| 2015/0094766 A1 | 4/2015 | Blain et al. |
| 2015/0094767 A1 | 4/2015 | Blain et al. |
| 2015/0119988 A1 | 4/2015 | Assell et al. |
| 2015/0164516 A1 | 6/2015 | Blain et al. |
| 2015/0164652 A1 | 6/2015 | Assell et al. |
| 2015/0190149 A1 | 7/2015 | Assell et al. |
| 2015/0196330 A1 | 7/2015 | Blain |
| 2015/0209096 A1 | 7/2015 | Gephart |
| 2015/0257770 A1 | 9/2015 | Assell et al. |
| 2015/0257773 A1 | 9/2015 | Blain |
| 2015/0327872 A1 | 11/2015 | Assell et al. |
| 2016/0051294 A1 | 2/2016 | Blain |
| 2016/0113692 A1 | 4/2016 | Knoepfle |
| 2016/0128739 A1 | 5/2016 | Blain et al. |

(56) References Cited

U.S. PATENT DOCUMENTS

| | | | |
|---|---|---|---|
| 2016/0128838 A1 | 5/2016 | Assell et al. | |
| 2016/0213481 A1 | 7/2016 | Blain | |
| 2016/0324549 A1 | 11/2016 | Blain | |
| 2017/0000527 A1 | 1/2017 | Blain et al. | |

FOREIGN PATENT DOCUMENTS

| | | | |
|---|---|---|---|
| DE | 201 12 123 | 9/2001 | |
| DE | 101 35 771 | 2/2003 | |
| DE | 10135771 A1 * | 2/2003 | ......... A61B 17/7064 |
| EP | 0 238 219 | 9/1987 | |
| EP | 0 322 334 | 6/1989 | |
| EP | 0 392 124 | 10/1990 | |
| EP | 0 610 837 | 8/1994 | |
| EP | 0 928 603 | 7/1999 | |
| EP | 1 201 202 | 5/2002 | |
| EP | 1 201 256 | 5/2002 | |
| EP | 2 919 717 | 9/2015 | |
| FR | 2 704 745 | 11/1994 | |
| FR | 2 722 980 | 2/1996 | |
| GB | 2 366 736 | 3/2002 | |
| JP | 62-270147 | 11/1987 | |
| JP | 10-179622 | 7/1998 | |
| JP | 2000-210297 | 8/2000 | |
| JP | 2004-508888 | 3/2004 | |
| JP | 2004-181236 | 7/2004 | |
| JP | 2007-503884 | 3/2007 | |
| JP | 2007-517627 | 7/2007 | |
| JP | 2007-190389 | 8/2007 | |
| JP | 2008-510526 | 4/2008 | |
| JP | 2009-533167 | 9/2009 | |
| JP | 2013-534451 | 9/2013 | |
| MX | 6012309 | 1/2007 | |
| WO | WO 93/014721 | 8/1993 | |
| WO | WO 94/004088 | 3/1994 | |
| WO | WO 97/047246 | 12/1997 | |
| WO | WO 98/048717 | 11/1998 | |
| WO | WO 99/023963 | 5/1999 | |
| WO | WO 00/038582 | 7/2000 | |
| WO | WO 00/053126 | 9/2000 | |
| WO | WO 01/030248 | 5/2001 | |
| WO | WO 02/045765 | 6/2002 | |
| WO | WO 02/065954 | 8/2002 | |
| WO | WO 02/096300 | 12/2002 | |
| WO | WO 03/101350 | 12/2003 | |
| WO | WO 2004/071358 | 8/2004 | |
| WO | WO 2005/020850 | 3/2005 | |
| WO | WO 2005/072661 | 8/2005 | |
| WO | WO 2006/023980 | 3/2006 | |
| WO | WO 2006/096803 | 9/2006 | |
| WO | WO 2009/021876 | 2/2009 | |
| WO | WO 2010/060072 | 5/2010 | |
| WO | WO 2010/122472 | 10/2010 | |
| WO | WO 2011/011621 | 1/2011 | |
| WO | WO 2012/007941 | 1/2012 | |
| WO | WO 2012/116266 | 8/2012 | |
| WO | WO 2013/022880 | 2/2013 | |
| WO | WO 2013/138655 | 9/2013 | |
| WO | WO 2014/078541 | 5/2014 | |
| WO | WO 2016/044432 | 3/2016 | |

OTHER PUBLICATIONS

3rd Party Lab Notebook, "Facet Cartilage Repair," dated May 20, 2003 in 2 pages.
ArthroTek, "CurvTek® Bone Tunneling System," Surgical Technique, 2000, pp. 6.
ArthroTek, "CurvTek® Bone Tunneling System," User's Manual, 2000, pp. 20.
Ash, H.E., "Proximal Interphalangeal Joint Dimensions for the Design of a Surface Replacement Prosthesis", School of Engineering, University of Durham, Proceedings of the Institution of Mechanical Engineers Part H Journal of Engineering in Medicine Feb. 1996, vol. 210, No. 2, pp. 95-108.
Beaman, MD et al., "Substance P Innervation of Lumbar Spine Facet Joints", SPINE, 1993, vol. 18, No. 8, pp. 1044-1049.
Butterman, et al., "An Experimental Method for Measuring Force on the Spinal Facet Joint: Description and Application of the Method", Journal of Biomechanical Engineering, Nov. 1991, vol. 113, pp. 375-386.
Cruess et al., "The Response of Articular Cartilage to Weight-Bearing Against Metal", The Journal of Bone and Joint Surgery, Aug. 1984, vol. 66-B, No. 4, pp. 592-597.
Dalldorf et al., "Rate of Degeneration of Human Acetabular Cartilage after Hemiarthroplasty", The Journal of Bone and Joint Surgery, Jun. 1995, vol. 77. No. 6, pp. 877-882.
E-mail from 3rd Party citing U.S. Appl. No. 60/721,909; U.S. Appl. No. 60/750,005 and U.S. Appl. No. 60/749,000, initial email dated May 11, 2009, reply e-mail dated May 18, 2009.
Frost, Harold M., "From Wolff's Law to the Utah Paradigm: Insights About Bone Physiology and Its Clinical Applications", The Anatomical Record, 2001, vol. 262, pp. 398-419.
King et al., "Mechanism of Spinal Injury Due to Caudocephalad Acceleration," Symposium on the Lumbar Spine, Orthopedic Clinic of North America, Jan. 1975, vol. 6, pp. 19-31.
Kurtz, PhD et al., "Isoelastic Polyaryletheretherketone Implants for Total Joint Replacement", PEEK Biomaterials Handbook, Ch. 14, 2012, pp. 221-226.
Meisel et al., "Minimally Invasive Facet Restoration Implant for Chronic Lumbar Zygapophysial Pain: 1-Year Outcomes", Annals of Surgical Innovation and Research (ASIR), 2014, vol. 8, No. 7, pp. 6.
Panjabi, PhD et al., "Articular Facets of the Human Spine: Quantitative Three-Dimensional Anatomy", SPINE, 1993, vol. 18, No. 10, pp. 1298-1310.
PARTEQ Innovations, "Facet Joint Implants & Resurfacing Devices," Technology Opportunity Bulletin, Tech ID 1999-012, Queen's University, Ontario Canada, pp. 2.
Ravikumar et al., "Internal Fixation Versus Hemiarthroplasty Versus Total Hip Arthroplasty for Displaced Subcapital Fractures of Femur—13 year Results of a Prospective Randomised Study", International Journal of the Care of the Injured (Injury), 2000, vol. 31, pp. 793-797.
Schendel et al., "Experimental Measurement of Ligament Force, Facet Force, and Segment Motion in the Human Lumbar Spine", Journal of Biomechanics, 1993, vol. 26, No. 4/5, pp. 427-438.
Tanno et al., "Which Portion in a Facet is Specifically Affected by Articular Cartilage Degeneration with Aging in the Human Lumbar Zygapophysial Joint?", Okajimas Folia Anatomica Japonica, May 2003, vol. 80, No. 1, pp. 29-34.
Official Communication in Australian Application No. 2005213459, dated Dec. 11, 2009.
Official Communication in Australian Application No. 2005213459, dated Dec. 15, 2010.
Official Communication in Australian Application No. 2011226832, dated Sep. 4, 2012.
Official Communication in Australian Application No. 2011226832, dated Oct. 31, 2012.
Official Communication in Australian Application No. AU2013237744, dated Sep. 2, 2014.
Notice of Acceptance in Australian Application No. AU2013237744, dated Apr. 23, 2015.
Official Communication in Australian Application No. AU2015205875, dated Apr. 2, 2016.
Official Communication in Australian Application No. AU2015205875, dated Jun. 15, 2016.
Official Communication in Canadian Application No. 2,555,355, dated Sep. 2, 2011.
Official Communication in Canadian Application No. 2,803,783, dated Sep. 29, 2014.
Official Communication in Canadian Application No. 2,803,783, dated Aug. 5, 2015.
Official Communication in Canadian Application No. 2,803,783, dated Jul. 7, 2016.
Official Communication in European Application No. 05712981.9, dated Jul. 24, 2007.

(56) References Cited

OTHER PUBLICATIONS

Official Communication in European Application No. 05712981.9, dated Mar. 10, 2008.
Official Communication in European Application No. 05712981.9, dated Apr. 6, 2009.
Official Communication in European Application No. 05712981.9, dated Jun. 15, 2010.
Official Communication in European Application No. 10178979.0, dated Mar. 14, 2011.
Official Communication in European Application No. 10178979.0, dated Nov. 13, 2012.
Official Communication in European Application No. 10178979.0, dated Aug. 5, 2013.
Official Communication in European Application No. 14175088.5, dated Sep. 8, 2014.
Official Communication in European Application No. 14175088.5, dated Nov. 18, 2015.
Official Communication in Japanese Application No. 2006-552309, dated May 25, 2010.
Official Communication in Japanese Application No. 2006-552309, dated Feb. 15, 2011.
Official Communication in Japanese Application No. 2010-221380, dated Feb. 15, 2011.
Official Communication in Japanese Application No. 2012-272106, dated Dec. 3, 2013.
Official Communication in Japanese Application No. 2012-272106, dated May 26, 2014.
Official Communication in Japanese Application No. 2012-272106, dated Feb. 23, 2015.
Official Communication in Japanese Application No. 2012-272106, dated Nov. 2, 2015.
International Search Report and Written Opinion in International Application No. PCT/US2005/003753, dated Dec. 5, 2006.
International Preliminary Report and Written Opinion in International App No. PCT/US2005/003753, dated Jan. 9, 2007.
Official Communication in European Application No. 08730413.5, dated Feb. 16, 2012.
Official Communication in European Application No. 14177951.2, dated Nov. 13, 2014.
International Search Report and Written Opinion in International Application No. PCT/US2008/054607, dated Jul. 10, 2008.
International Preliminary Report on Patentability in International Application No. PCT/US2008/054607, dated Sep. 3, 2009.
Official Communication in Australian Application No. 2011292297, dated Jul. 10, 2013.
Official Communication in Australian Application No. 2014277721, dated Sep. 8, 2016.
Official Communication in Australian Application No. 2014277721, dated Jan. 9, 2017.
Official Communication in European Application No. 11818586.7, dated Nov. 6, 2014.
Official Communication in European Application No. 11818586.7, dated Feb. 3, 2017.
Official Communication in Japanese Application No. 2013-524882, dated Mar. 2, 2015.
Official Communication in Japanese Application No. 2013-524882, dated Nov. 16, 2015.
Official Communication in Japanese Application No. 2015-242990, dated Dec. 12, 2016.
International Search Report and Written Opinion in International Application No. PCT/US2011/047432, dated Dec. 12, 2011.
International Preliminary Report on Patentability in International Application No. PCT/US2011/047432, dated Feb. 28, 2013.
Official Communication in Australian Application No. AU2012222229, dated Aug. 21, 2015.
Official Communication in Australian Application No. AU2012222229, dated May 11, 2016.
Official Communication in Australian Application No. AU2012222230, dated Aug. 21, 2015.
Official Communication in European Application No. EP12749447.4, dated Jan. 4, 2017.
Official Communication in European Application No. 12749251.0, dated Jan. 4, 2017.
Official Communication in Japanese Application No. JP 2013-555591, dated Jan. 4, 2016.
Official Communication in Japanese Application No. JP 2013-555592, dated Dec. 7, 2015.
Official Communication in Japanese Application No. JP 2013-555592, dated Aug. 8, 2016.
International Search Report in International Application No. PCT/US2012/026470, dated May 30, 2012.
International Preliminary Report on Patentability and Written Opinion in International Application No. PCT/US2012/026470, dated Sep. 6, 2013.
International Search Report and Written Opinion in International Application No. PCT/US2012/026472, dated Jun. 20, 2012.
International Preliminary Report on Patentability and Written Opinion in International Application No. PCT/US2012/026472, dated Mar. 12, 2014.
Official Communication in European Application No. 14774714.1, dated Oct. 21, 2016.
International Search Report and Written Opinion in International Application No. PCT/US2014/019302, dated May 18, 2015.
Official Communication in European Application No. 14776445.0, dated Nov. 7, 2016.
International Search Report and Written Opinion in International Application No. PCT/US2014/019325, dated Jun. 17, 2014.
International Preliminary Report on Patentability and Written Opinion in International Application No. PCT/US2014/019325, dated Sep. 24, 2015.
Official Communication in European Application No. 14850082.0, dated Aug. 31, 2016.
International Search Report and Written Opinion in International Application No. PCT/US2014/056598, dated Dec. 29, 2014.
International Preliminary Report on Patentability and Written Opinion in International Application No. PCT/US2014/056598, dated Apr. 7, 2016.
International Search Report and Written Opinion in International Application No. PCT/US2015/050441, dated Dec. 28, 2015.
International Search Report and Written Opinion in International Application No. PCT/US2016/013062, dated Mar. 16, 2016.
International Search Report in International Application No. PCT/CA2002/000193 filed Feb. 15, 2002, dated Jun. 18, 2002.
International Search Report and Written Opinion in International Application No. PCT/US2004/028094, dated May 16, 2005.
International Preliminary Report on Patentability in International Application No. PCT/US2004/028094, dated Feb. 25, 2013.
International Search Report in International Application No. PCT/US2005/000987 filed Jan. 13, 2005, dated May 24, 2005.
International Preliminary Report on Patentability in International Application No. PCT/US2005/000987 filed Jan. 13, 2005, dated Jan. 17, 2006.

\* cited by examiner

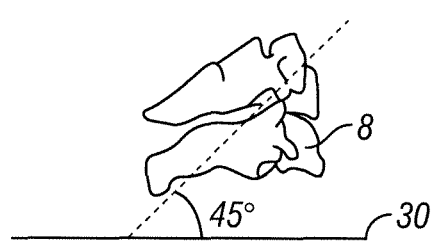
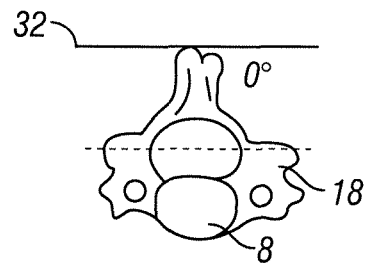
FIG. 4A             FIG. 4B
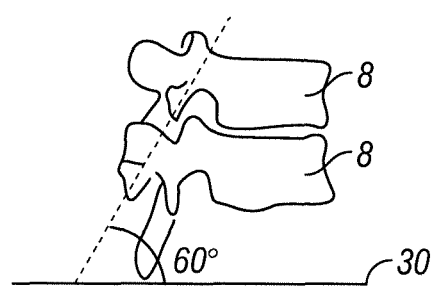
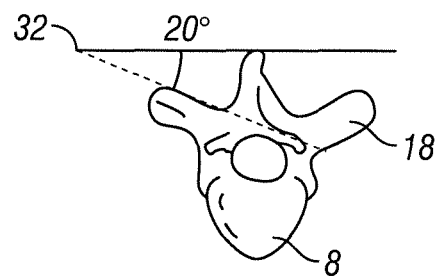
FIG. 5A             FIG. 5B
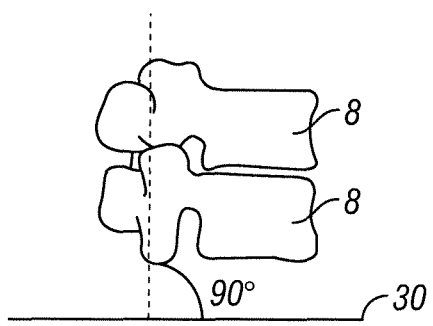
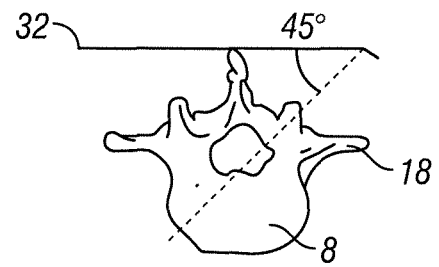
FIG. 6A             FIG. 6B

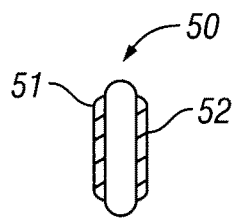
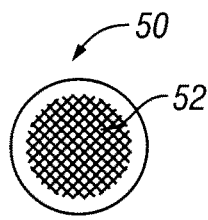
FIG. 14A  FIG. 14B
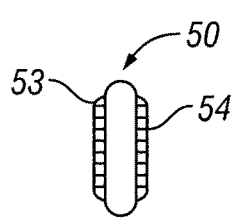
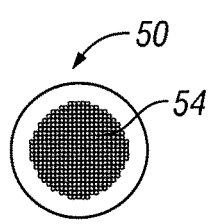
FIG. 15A  FIG. 15B
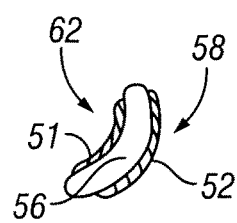
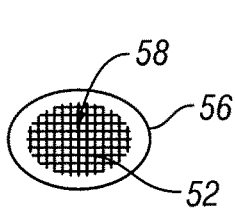
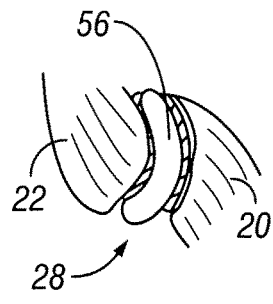
FIG. 16A  FIG. 16B  FIG. 17
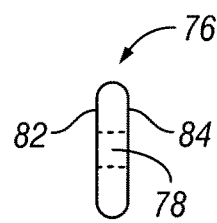
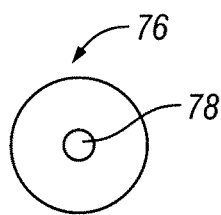
FIG. 18A  FIG. 18B
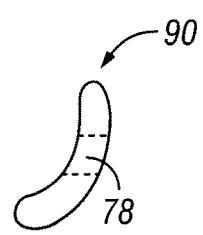
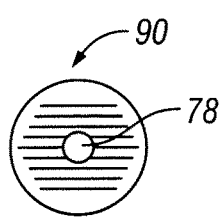
FIG. 19A  FIG. 19B

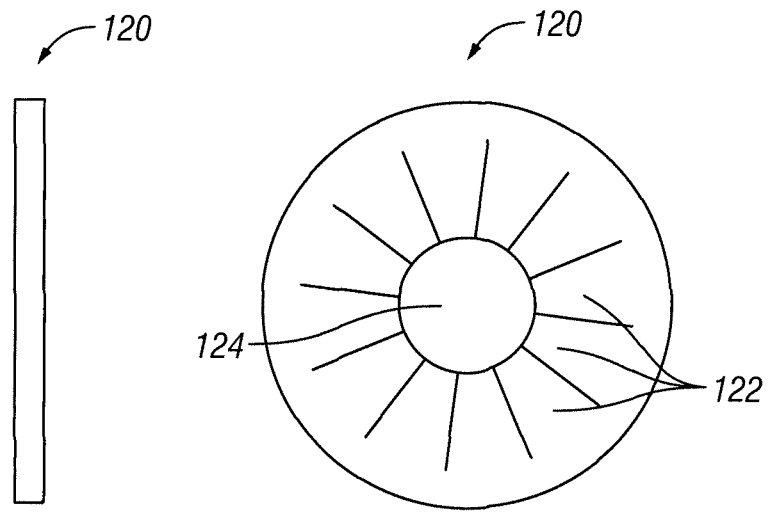
FIG. 29A  FIG. 29B
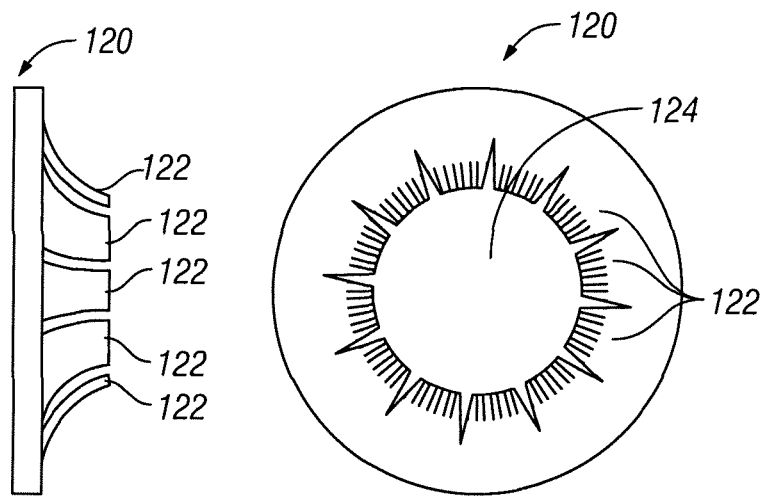
FIG. 30A  FIG. 30B

IMPLANT AND METHOD FOR FACET IMMOBILIZATION

CROSS-REFERENCE TO RELATED APPLICATIONS

The present application is a divisional of U.S. patent application Ser. No. 12/106,248, filed Apr. 18, 2008, now U.S. Pat. No. 9,504,583, which is a continuation-in-part of U.S. patent application Ser. No. 10/865,073, filed on Jun. 10, 2004, now U.S. Pat. No. 7,846,183, the contents of which are incorporated by reference herein in their entireties.

BACKGROUND

Field

The present invention relates to an implant and method for immobilizing a vertebral facet joint.

Background

Traumatic, inflammatory, and degenerative disorders of the spine can lead to severe pain and loss of mobility. For example, back and spinal musculoskeletal impairments are significant causes of lost work productivity in the United States. Pain as a result of some type of spinal impairment may have its source in a variety of pathologies or clinical conditions.

As shown in FIG. 1, the vertebral column 2 of the spine includes a series of alternating vertebrae 4 and fibrous discs 6 that provide axial support and movement to the upper portions of the body. The vertebral column 2 typically includes thirty-three vertebrae 4, with seven cervical (C1-C7), twelve thoracic (T1-T12), five lumbar (L1-15), five fused sacral (S1-S5) and four fused coccygeal vertebrae.

FIGS. 2A and 2B depict a typical thoracic vertebra. Each vertebra includes an anterior body 8 with a posterior arch 10. The posterior arch 10 has two pedicles 12 and two laminae 14 that join posteriorly to form a spinous process 16. Projecting from each side of the posterior arch 10 is a transverse 18, superior 20 and inferior articular process 22. The facets 24, 26 of the superior 20 and inferior articular processes 22 form facet joints 28 where they align with the articular processes of the adjacent vertebrae, as shown in FIGS. 3A and 3B. The facet joints are true synovial joints, with cartilaginous surfaces and a joint capsule.

The orientation of the facet joints vary, depending on the level of the vertebral column. FIGS. 4A to 6B depict the orientations of the facet joints at different levels of the vertebral column. In the C1 and C2 vertebrae (not shown), the facet joints are substantially parallel to the transverse plane.

In the C3 to C7 vertebrae shown in FIGS. 4A and 4B, the facets are oriented at an approximately 45-degree angle to the transverse plane 30 and are substantially parallel to the frontal plane 32. This orientation allows the facet joints of the cervical vertebrae to flex, extend, laterally flex, and rotate. The 45-degree angle orientation with respect to the transverse plane 30 allows the facet joints of the cervical spine to guide the movement of the cervical vertebrae without limiting such movement.

FIGS. 5A and 5B depict the thoracic vertebrae, which include facets oriented at an approximately 60-degree angle to the transverse plane 30 and an approximately 20-degree angle to the frontal plane 32. This orientation is capable of allowing lateral flexion and rotation, but only limited flexion and extension.

FIGS. 6A and 6B illustrate the lumbar region, where the facet joints are oriented at approximately 90-degree angles to the transverse plane 30 and an approximately 45-degree angle to the frontal plane 32. The lumbar vertebrae allow flexion, extension and lateral flexion of the lumbar region, but little, if any, rotation because of the 90-degree orientation of the facet joints in the transverse plane. The actual range of motion along the vertebral column can vary considerably with each individual vertebra.

In addition to guiding movement of the vertebrae, the facet joints also contribute to the load-bearing ability of the vertebral column. For example, facet joints can bear up to 30% of the load on the spine in some positions of the vertebral column as described, e.g., in King et al., Mechanism of Spinal Injury Due to Caudocephalad Acceleration, Orthop. Clin. North Am., 6:19 (1975). The facet joints may also play a role in resisting shear stresses between the vertebrae. Over time, these forces acting on the facet joints can cause degeneration and arthritis.

One source of back and spine pain is related to degeneration of the facets of the spine or facet arthritis. Bony contact or grinding of degenerated facet joint surfaces between two vertebrae may play a role in some pain syndromes. Such degenerative problems with the facet joints are often treated by fusing the two adjacent vertebrae together. By performing this surgical procedure, the relative motion between the two adjacent vertebrae is effectively stopped. This fusion procedure significantly reduces relative motion of the facets between the adjacent vertebrae. However, the facets between fused vertebrae may still exhibit some relative motion as the vertebral column is subjected to overall movement and various stresses. Such motion can lead to further problems, such as pain, arising from the degenerative facet joint.

Often, the facet joints between fused vertebrae are not treated as part of the fusion procedure. In certain procedures, the facets may simply be screwed together. However, because there is cartilage in the facet joints, the joints may not fuse and can still be a source of further discomfort.

Accordingly, there is a need to address the clinical concerns raised by degenerative facet joints, and to immobilize such facet joints when adjacent vertebrae are fused together.

SUMMARY

Various implants have been proposed for addressing facet degeneration by restoring motion, and often require bony resection to be placed within the spine. Alternatively, facet joints are often left untouched when adjacent vertebrae are fused together, which substantially reduces motion within the facet joints between the vertebrae. However, even slight motion within the degenerated facet joints can lead to further discomfort and pain.

Embodiments of the present invention provide a method and device for immobilizing a facet joint. The method and device allow maintenance of the relative spacing between the facets within the facet joint, while allowing each of the adjacent articular surfaces of the facet joint to fuse to an implant provided between the facets. Such immobilization of the facet joint can alleviate the bone on bone contact that is common in degenerative facet joints and which may be a source of pain or discomfort even when the adjacent vertebrae are fused together.

In one aspect, embodiments of the invention provide a device for inhibiting movement at a facet joint which includes an implant. The faces of the implant are shaped such that they can be secured to the adjacent articular surfaces of the facet joint. The implant is dimensioned to fit substantially within the joint capsule of the facet joint. For example, the implant may have an average diameter that is between about 5 mm and about 25 mm, or between about 10 mm and about 20 mm.

The implant can be formed using a polymer, including but not limited to polyetheretherketone (PEEK), polyetherketoneketone (PEKK), or polyethylene; a ceramic including but not limited to zirconia, alumina, or silicon nitride; or a metal including but not limited to titanium, a titanium alloy, cobalt chromium, or a stainless steel. The implant can also be formed using other metals or metal alloys, an allograft, an autograft, or a combination of two or more of the above materials. The faces of the implant can be roughened or porous to improve bonding, friction, adherence, and/or osteoincorporation with the articular surfaces. For example, the implant can be made partially or entirely from a partially-sintered powdered metal.

The implant preferably has a thickness that is approximately the same as the normal anatomic spacing between the facets of the facet joint or slightly larger. For example, the thickness of the implant may be between about 0.5 mm and about 3 mm, or between about 1 mm and about 2 mm.

The implant may be configured to be bonded to the articular surfaces of the facets using an adhesive or a sealant. Alternatively, the device may include an anchoring arrangement configured to maintain the implant in a fixed position relative to the adjacent articular surfaces of the facet joint. The anchoring arrangement can also provide a compressive force between the implant and the articular surfaces to better immobilize the facet joint. For example, the anchoring arrangement is preferably configured to pass through holes formed in the implant and articular processes associated with the facet joint. The anchoring arrangement is preferably a rigid fastener such as a threaded retainer, e.g., a threaded bolt, or a rod or cylinder which includes a flange, a retainer ring or disc, or a threaded nut provided at one or both ends. The anchoring arrangement can also be curved or bent along its primary axis.

In a further aspect, a method of treating vertebral dysfunction by immobilizing a facet joint is provided, in which an incision is made above the facet joint and the facet joint capsule is opened. Some or all of the cartilage within the facet joint is removed, and the articular surfaces may optionally be roughened. An implant is then placed within the facet joint between the articular surfaces and secured therein. In certain embodiments, the implant is secured using an adhesive or a sealant.

In further embodiments, an anchoring arrangement is provided to secure the implant to the articular processes and immobilize the facet joint. For example, a hole can be formed through the implant and the articular processes of the facet joint. A retaining member, which preferably has the shape of a rod or cylinder, is then inserted through the holes, and one or more fasteners are provided at the ends of the retaining member to secure the articular processes and implant together. The fasteners can include, for example, a threaded nut, a retainer ring with a set screw, a disc with a friction fit, or a flange.

After the facet joint is immobilized, the incision is closed and allowed to heal.

BRIEF DESCRIPTION OF THE DRAWINGS

Further objects, features and advantages of the invention will become apparent from the following detailed description taken in conjunction with the accompanying figures showing illustrative embodiments, results and/or features of the present invention, in which:

FIGS. 4A and 4B are schematic side and superior views, respectively, of a facet joint in the cervical vertebrae;

FIGS. 5A and 5B are schematic side and superior views, respectively, of a facet joint in the thoracic vertebrae;

FIGS. 6A and 6B are schematic side and superior views, respectively, of a facet joint in the lumbar vertebrae;

FIGS. 14A and 14B are schematic views of a facet joint implant having a disc shape with roughened surfaces;

FIGS. 15A and 15B are schematic views of a facet joint implant having a disc shape with porous surfaces;

FIGS. 16A and 16B are schematic views of a facet joint implant having a bent disc shape with roughened surfaces;

FIG. 17 is a schematic view of the implant of FIG. 16A implanted in a facet joint;

FIGS. 18A and 18B are schematic views of a facet joint implant which includes a centrally located hole;

FIGS. 19A and 19B are schematic views of a facet joint implant having a curved disc shape which includes a centrally located hole;

FIGS. 29A and 29B are friction fit retaining rings shown in a relaxed state;

FIGS. 30A and 30B depict the retaining rings of FIGS. 29A and 29B in an expanded state.

Figure 1:
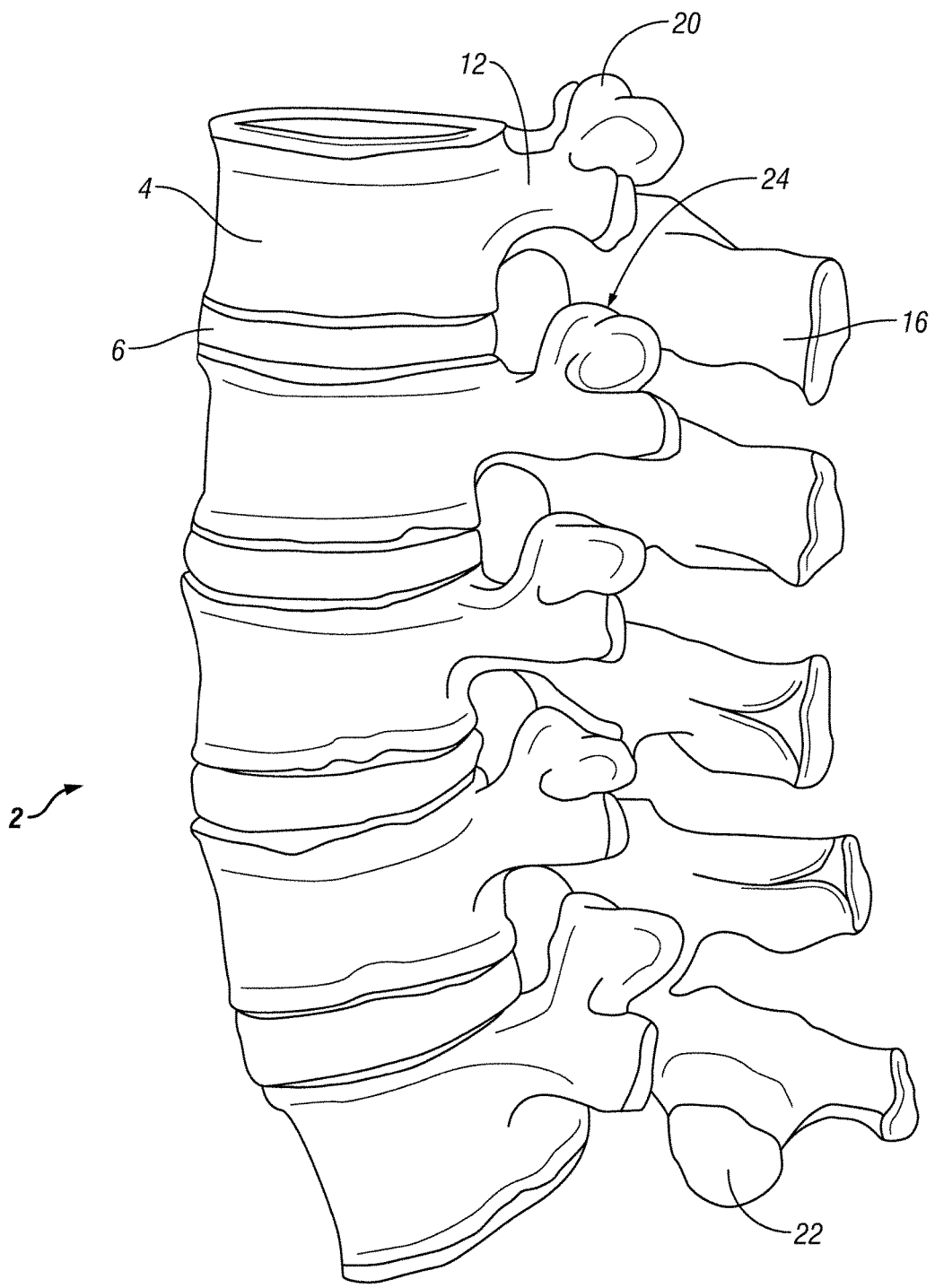
FIG. 1 is a lateral elevational view of a portion of the vertebral column.
Figure 2A:
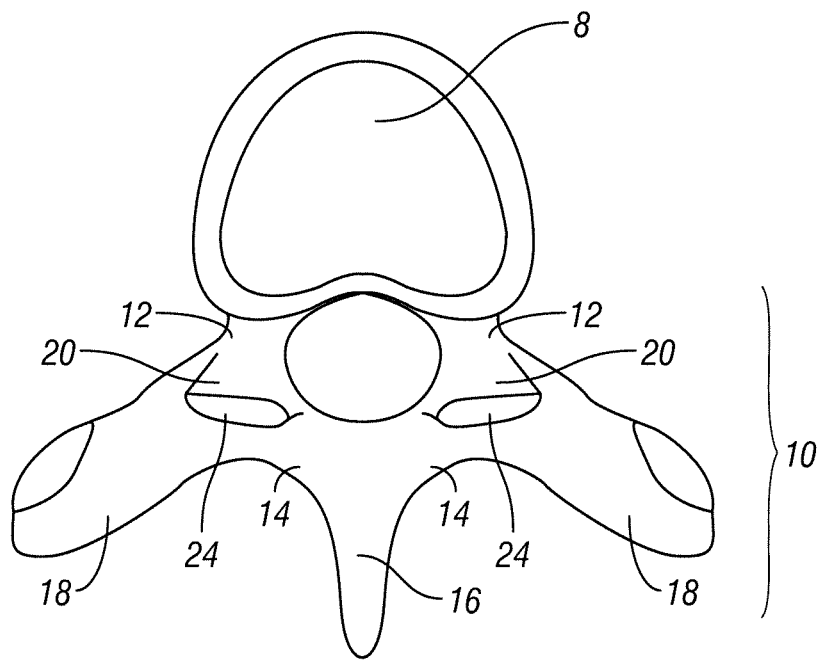
FIGS. 2A and 2B are schematic superior and side views, respectively, of an isolated thoracic vertebra.
Figure 2B:
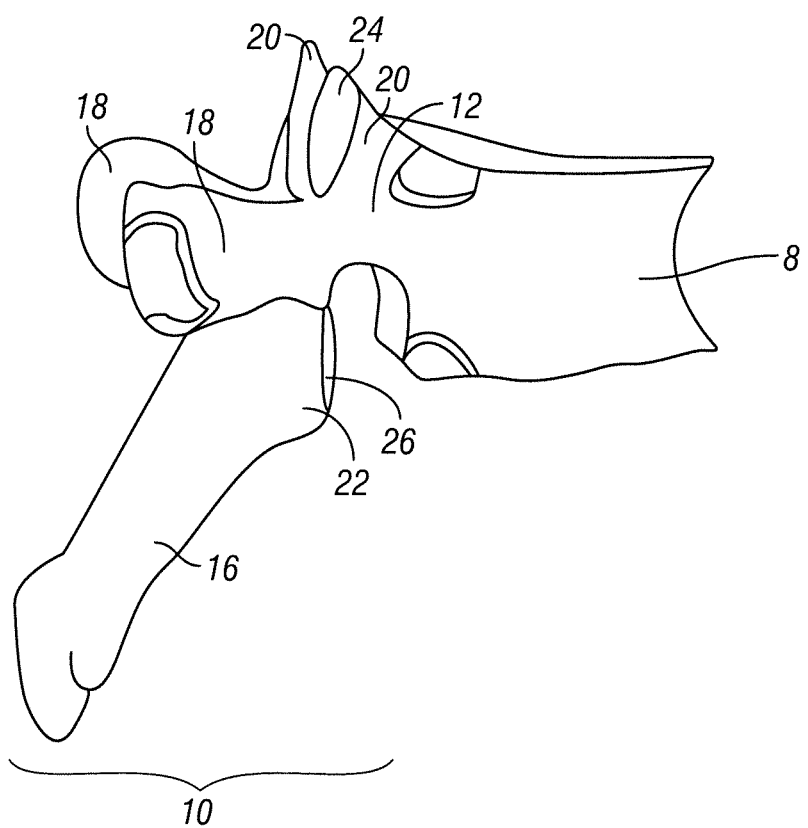
Figure 3A:
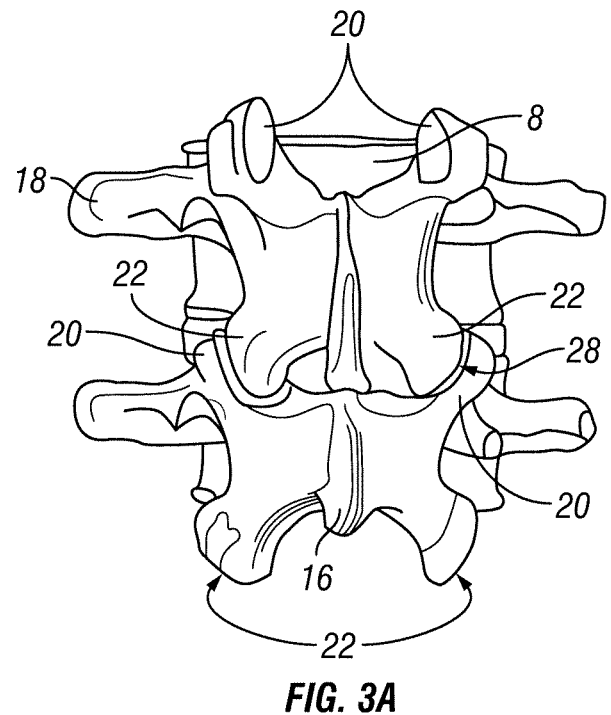
FIGS. 3A and 3B are schematic posterior and posterior-oblique elevational views, respectively, of a portion of the vertebral column.
Figure 3B:
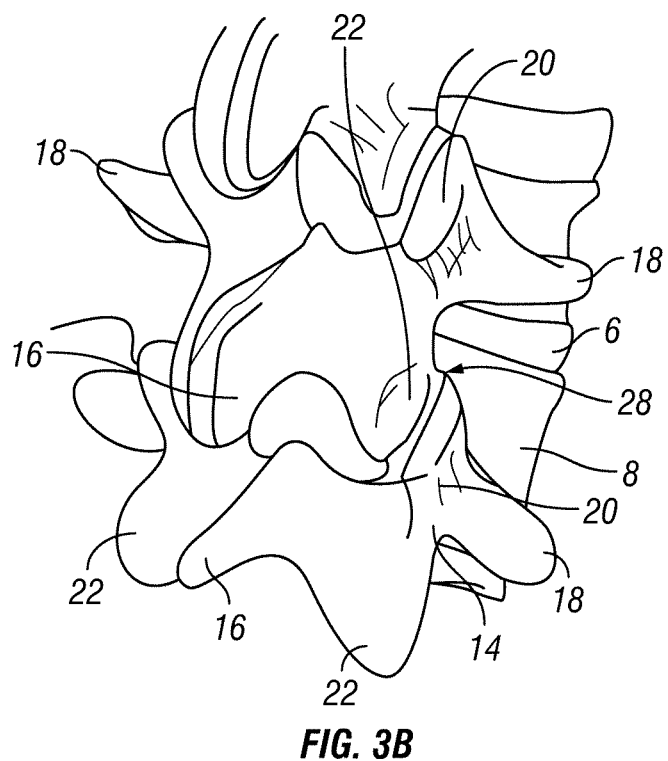

Throughout the drawings, the same reference numerals and characters, unless otherwise stated, are used to denote like features, elements, components, or portions of the illustrated embodiments. Moreover, while the present invention will now be described in detail with reference to the figures, it is done so in connection with the illustrative embodiments and is not limited by the particular embodiments illustrated in the figures.

DETAILED DESCRIPTION

Figure 7A:
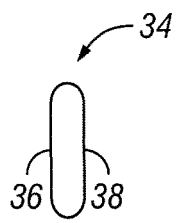
FIGS. 7A and 7B are schematic views of a facet joint implant having a circular disc shape.
Figure 7B:
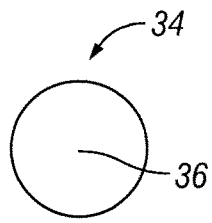

In one aspect, embodiments of the present invention provide a device for immobilizing a facet joint, and which can further maintain a spacing between the two facets of the immobilized facet joint. As shown in FIGS. 7A and 7B, the device includes an implant 34 with two faces: a first face 36 adapted to contact the articular surface of one facet of the facet joint and a second face 38 adapted to contact the articular surface of the other facet.

The implant can be formed from any of a variety of materials known in the art, including but not limited to a polymer such as polyetheretherketone (PEEK), polyetherketoneketone (PEKK), or polyethylene. Alternatively, the implant can be formed from a ceramic such as zirconia, alumina, or silicon nitride. The implant may also be formed from a metal including, but not limited to, titanium, a titanium alloy, cobalt chromium, or a stainless steel. The implant can also be formed from a wafer of allograft material or autograft material, which can promote growth of bone tissue from the facets into the implant. The implant can also be formed from a combination of two or more of the materials cited herein.

Figure 8:
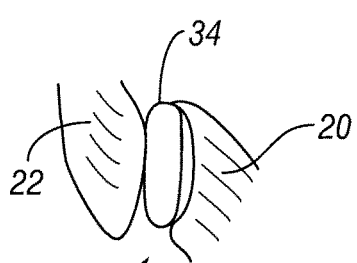
FIG. 8 is a schematic view of the implant of FIG. 7A implanted in a facet joint.
Figure 9A:
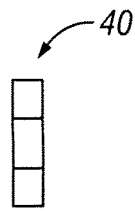
FIGS. 9A and 9B are schematic views of a facet joint implant having an octagonal disc shape.
Figure 9B:
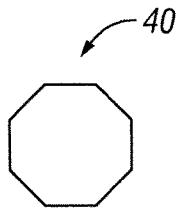

In one embodiment, the implant 34 has a generally circular profile and is sized to fit substantially within the joint capsule of the facet joint 28. FIG. 8 illustrates the implant 34 of FIGS. 7A and 7B positioned in a facet joint to be immobilized. In other embodiments, the implant can have any of a variety of profiles, including but not limited to square, rectangle, oval, star, polygon or a combination or variation thereof. For example, an octagonal implant 40 is shown in FIGS. 9A and 9B. The shape of a particular implant can be selected based on radiographic or other visualization of the articular processes and/or the joint capsule. The shape of the implant is preferably selected so the two faces contact a substantial portion of the articular surfaces of the two facets of the facet joint.

In one embodiment, the implant has a diameter between about 4 mm and about 30 mm. In another embodiment, the implant has a diameter between about 5 mm and about 25 mm. In still another embodiment, the implant has a diameter between about 10 mm and about 20 mm. If the implant is not circular in shape, the diameter can refer to the longest dimension measured across one of the two faces thereof. The diameter of a particular implant can be selected based on the size of the articular surfaces in the facet joint to be immobilized, which varies with location in a particular vertebral column. Preferably, the diameter of the implant should not be so large that the implant protrudes significantly beyond the edges of the articular surfaces, and is large enough such that the faces of the implant contact a substantial portion of the articular surfaces. Further, the implant should not protrude past the periphery of the facet joint closest to the vertebral column, as such protrusion may interfere with a disc or the spinal cord.

The implant preferably has a thickness approximately the same as the anatomic spacing between two facets of the facet joint to be immobilized. For example, the implant generally has a thickness between about 0.5 mm and about 3.0 mm. In certain embodiments, the implant has a thickness between about 1 mm and about 2 mm. In further embodiments, the implant has a thickness between about 0.5 mm and about 1.5 mm. The thickness of the implant may also be slightly larger than the anatomic spacing between two facets of the facet joint. A thicker implant can improve contact between the implant faces and the articular surfaces when the implant 34 is placed between the facets 20, 222 as shown, for example, in FIG. 8.

Figure 10A:
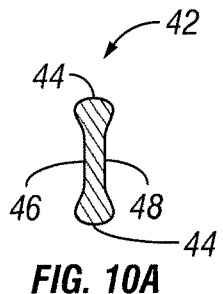
FIGS. 10A and 10B are schematic views of a facet joint implant having a biconcave disc shape.
Figure 10B:
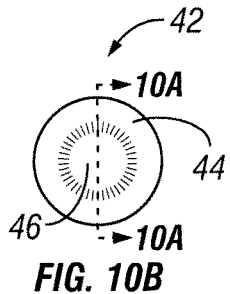
Figure 11A:
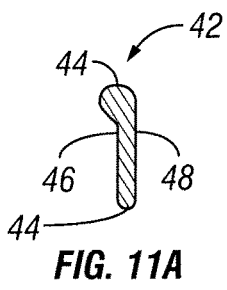
FIGS. 11A and 11B are schematic views of a facet joint implant having a single-face variable thickness disc shape.
Figure 11B:
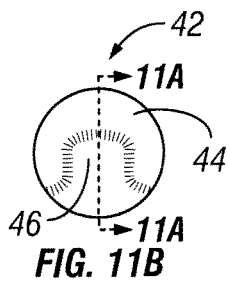

The implant can be configured to provide an improved fit with the articular process and/or joint capsule. In certain embodiments, the thickness of a particular implant is non-uniform. For example, in FIGS. 10A and 10B, the thickness of the implant 42 is increased around the entire outer edge 44 along both faces 46, 48. In FIGS. 11A and 11B, only a portion of the edge 44 on one face 46 of the implant 42 has a thickness that is greater than the thickness of a central region, and, optionally, also thicker than the typical anatomic spacing between two facets of a facet joint. Such variations in thickness of the implant may also resist lateral displacement of the implant out of the facet joint.

Figure 12A:
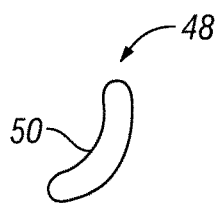
FIGS. 12A and 12B are schematic views of a facet joint implant having a curved disc shape.
Figure 12B:
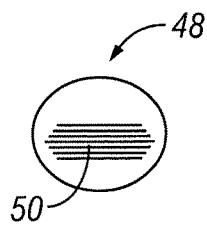
Figure 13:
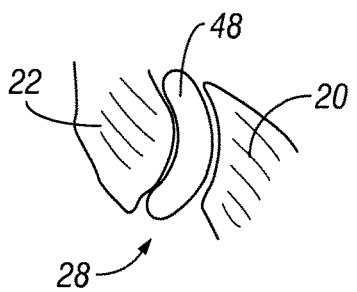
FIG. 13 is a schematic view of the implant of FIG. 12A implanted in a facet joint.

In certain embodiments, the implant may also be shaped to better conform to the shape of the articular surfaces of a facet joint. For example, the implant 49 shown in FIGS. 12A and 12B has a bend, angle or curve 50 to more closely match the natural shape of an articular facet. FIG. 13 depicts the implant 49 shown in FIGS. 12A and 12B positioned in a facet joint. The implant may be rigid with a preformed bend. Alternatively, the implant may be sufficiently malleable that it will conform to some degree to the specific configuration of the adjacent facet surfaces when placed between them.

In embodiments of the present invention, the facet joint capsule is incised and at least a portion of the cartilage is removed from the joint space between the facets before the implant is placed therein. Preferably, enough of the cartilage in the facet joint is removed such that all or a substantial portion of the articular surfaces of the facets are exposed. One or both of the adjacent articular surfaces can be roughened to improve contact with the implant and reduce slippage between the implant faces and the articular surfaces of the facets.

Preferably, at least a portion of each face of the implant is porous and/or roughened. In one embodiment, shown in FIGS. 14A and 14B, at least a portion of the surfaces 51, 52 of the implant 50 are roughened. Such roughening can improve adhesion and reduce slippage between the surfaces 51, 52 and the articular faces of the facet joint.

In a further embodiment, at least a portion of the surfaces 53, 54 of the implant 50 are porous as shown in FIGS. 15A and 15B. The porous surfaces 53, 54 can be created in any of a variety of conventional techniques, such as by applying sintered beads or spraying plasma onto the implant surface. Alternatively, the implant 50 can be made partially or entirely from a porous material such as a partially-sintered powder metal form. For example, porous surfaces 53, 54 can allow bone to grow into or attach to the surfaces 53, 54 of the implant 50, thus securing the implant 50 to the bone in the adjacent facets.

A curved implant 56 is shown in FIGS. 16A and 16B. The implant has a convex face 58 with a roughened surface 52, and a concave face 62 with a roughened face 51. The implant 56 can be placed in the facet joint 28 between facets 20, 22, as shown in FIG. 17. The implant 56 is shaped to provide good contact with the articular surfaces of the facets 20, 22. The roughened faces 51, 52 of the implant 56 can promote friction and/or adhesion between the articular surfaces and the implant 56, promoting immobilization of the facet joint 28. The roughened faces 51, 52 of the implant 56 (or, alternatively, porous faces of the implant if provided) may also promote growth of bone from the articular surfaces of the facets 20, 22 into the implant to fuse the facet joint. As shown in FIG. 17, the spacing between the facets 20, 22, can be substantially the same when the implant 56 is inserted as the spacing before fusion of the joint 28 using the implant 56.

In certain embodiments of the invention, the implant is maintained between the two facets of the facet joint by taking advantage of the joint capsule and/or other body tissue surrounding the facet joint to limit the migration of the implant out of the facet joint. For example, the shape of the implant itself may be capable of resisting displacement of the implant from its position generally between the facet joint surfaces. A concave or biconcave configuration, such as that shown in FIGS. 10A and 10B, may resist displacement of the implant by providing an increased thickness at the periphery of the implant that requires a larger force and/or greater distraction of facet joint surfaces in order to cause displacement. Surface treatments or texturing of the implant can also be used to maintain the implant against the articular surfaces of the facet joint, as described herein. Further, a combination of disc configuration, surface texturing, and existing body tissue or structures can be used to maintain the position of the implant between the facets of the facet joint to be immobilized.

In one embodiment, an adhesive or sealant, such as a cyanoacrylate, polymethylmethacrylate, or another biocompatible adhesive, is used to bond the faces of the implant to the adjacent articular surfaces of the facet joint. Such bonding can promote fusion of the facet joint. In a further embodiment, bone growth facilitators, electrical current, or other conventional techniques may be used to accelerate osteoincorporation of textured or porous anchoring surfaces of the implant.

In further embodiments, the device further includes an anchoring arrangement configured to secure the implant in a fixed position relative to the adjacent facets. The anchoring arrangement preferably provides a compressive force between the implant and the facets to promote adhesion and/or osteoincorporation of the implant with the articular surfaces of the facets.

Figure 20:
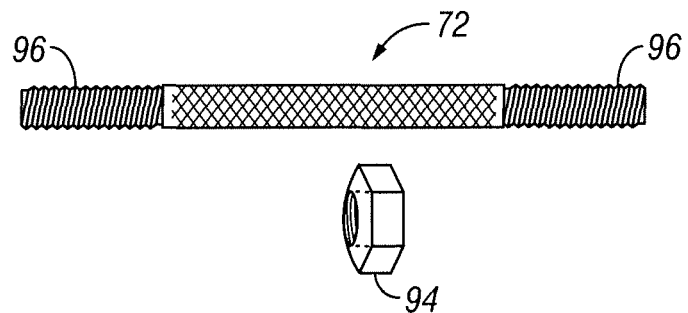
FIG. 20 depicts a retaining member which in the shape of a rod or cylinder with threaded ends adapted to accept threaded nuts.

In one embodiment of the invention, a hole 78 is provided through the implant 76 between opposite faces 82, 84, as shown in FIGS. 18A and 18B. Alternatively, the hole 78 can be provided through a curved implant 90, as shown in FIGS. 19A and 19B. The anchoring assembly includes a retaining member 72, which can have the shape of a rod or cylinder and is preferably made from a rigid material, as shown in FIG. 20. The anchoring assembly further includes two threaded nuts 94 which are configured to engage with threaded ends 96 of the retaining member 72.

Figure 21:
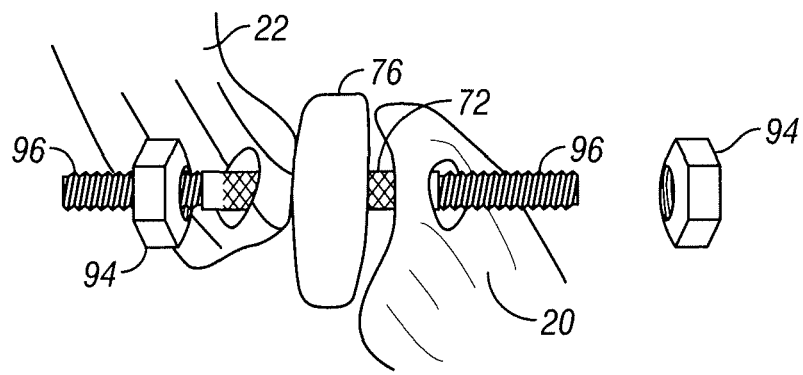
FIG. 21 depicts the retaining member of FIG. 20 which is used to affix the implant to the articular processes of a facet joint using threaded nuts.

A hole is formed through both articular processes 20, 22 of the facet joint to be immobilized or fused, as shown in FIG. 21. The implant 76 is placed between the facets and the retainer member 72 is inserted through the hole in each articular process 20, 22 and through the hole 78 in the implant 76, also shown in FIG. 20. Each nut 94 can then be threaded onto a threaded end 96 of the retaining member 72, and tightened to secure the articular processes 20, 22 to the implant 76, and to provide a compressive force between the facets and the implant 76. Such force can provide substantial immobilization of the facet joint and/or help promote osteoincorporation of the implant 76 with the articular surfaces of the facet joint. The threaded portion 96 is preferably made from titanium, a titanium alloy, cobalt chromium, a stainless steel, another metal alloy, or a combination of two or more such materials.

The diameter of the hole 78 in the implant 76 and the diameters of the holes in the articular processes 20, 22 are preferably at least slightly larger than the diameter of the retainer member 72. This allows the retainer member 72 to be easily inserted through the holes, and can also allow the implant 76 and the articular processes 20, 22 to move freely with respect to the retainer member 72 when the nuts 94 are tightened onto the threaded ends 96. This can assist in providing compressive forces between the faces of the implant 76 and the adjacent facet surfaces when the nuts 94 are tightened on the retainer member 72.

The hole 78 can be formed in the implant 76 before it is inserted into the facet joint. Alternatively, the hole 78 can be formed together with the holes through the articular processes 20, 22 after the implant 76 is placed in the facet joint. Such holes can be formed by drilling, by using a punch, or by other conventional techniques suitable for creating a hole in the bone and implant materials.

The cross-sectional shape of the retaining member 72 can be selected from a variety of shapes, including but not limited to circles, ovals, squares, rectangles, other polygons, or other shapes. A circular shape is preferred to better conform to the threaded ends 96 and to provide a close fit with the drilled or punched holes in the articular processes 20, 22. The retaining member 72 generally has a diameter between about 0.25 mm and about 2 mm, or between about 0.5 mm and about 1.25 mm, or preferably between about 0.75 mm and about 1.25 mm. The diameter of the retaining member 72 may optionally vary along its length. The diameter of a particular retaining member 72 may be selected based on the facet joint being immobilized. For example, a larger diameter can be used for immobilizing facet joints in the lower vertebrae (e.g., lumbar vertebrae) which tend to have larger facets. Similarly, a smaller diameter can be used for immobilizing facet joints in the upper vertebrae (e.g., cervical vertebrae) which tend to have smaller facets.

The retaining member 72 has a length that is generally between about 5 mm and about 60 mm, or between about 10 mm and about 40 mm. The retaining member 72 can have a length of about 20 mm to about 30 mm. The length of a particular retaining member 72 may be selected based on the facet joint being immobilized. For example, a longer retaining member 72 can be used for immobilizing facet joints in the lower vertebrae (e.g., lumbar vertebrae) which tend to have thicker articular processes 20, 22. Similarly, a shorter retaining member 72 can be used for immobilizing facet joints in the upper vertebrae (e.g., cervical vertebrae) which tend to have thinner or smaller articular processes 20, 22. In general, it is preferable that the ends of the retaining member 72 do not protrude too far from the surfaces of the articular processes 20, 22 when inserted into the holes therethrough, but the retaining member 72 should be long enough to allow engagement of the nuts 94 onto the threaded ends 96.

Figure 22:
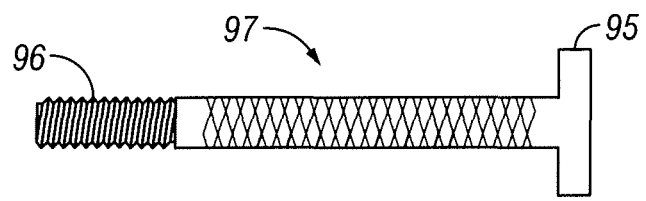
FIG. 22 depicts a retaining member which in the shape of a rod or cylinder with one threaded end adapted to accept a threaded nut and a flange provided at the opposite end.

In a further embodiment, shown in FIG. 22, the retaining member 97 is provided with a flange 95 at or near one end, and a single threaded end 96 at the opposite end. For example, the retaining member 97 can be a bolt having suitable dimensions and made from a suitable material. The threaded end 96 can be inserted through holes in the implant 76 and articular processes 20, 22, and a single nut 94 can be threaded onto the threaded end 96 to immobilize the facet joint and optionally provide a compressive force across the joint. The flange 95 is preferably larger in diameter than the hole diameters, such that it can engage one of the articular processes 20, 22. The flange 96 can be provided in any of a variety of shapes. For example, the side of the flange 95 closest to the threaded end 96 can be shaped to approximately conform to the outer surface of the articular process around the hole therethrough, to provide better contact and a more uniform force between the flange 95 and the articular process.

Figure 23A:
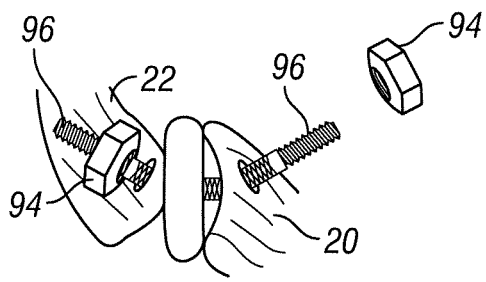
FIG. 23A depicts a curved retaining member which is used to affix the implant to the articular processes of a facet joint together with threaded nuts.

In another embodiment, the retaining member 72 of the anchoring assembly has a bend or a curve along the main axis, as shown in FIG. 23A. The bend or curve can provide a better orientation for the nuts 94 with respect to the articular processes 20, 22 for certain facet joints. For example, a curved retaining member 72 may allow the nuts to be positioned approximately flush with an outer surface of the articular processes 20, 22 when the nuts 94 are threaded onto the threaded ends 96.

Figure 23B:
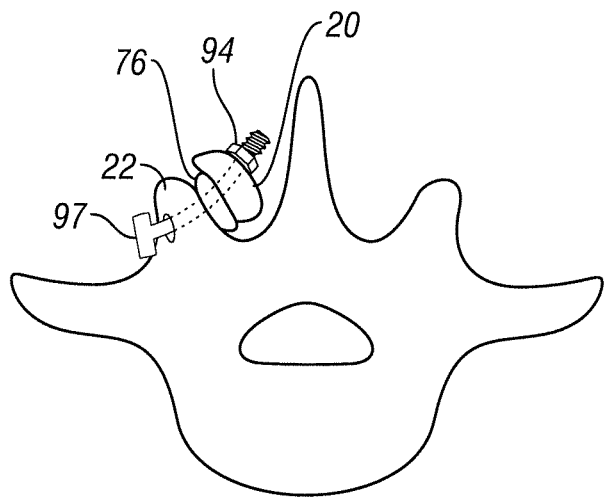
FIG. 23B depicts a retaining member which is a curved bolt that is used to affix the implant to the articular processes of a facet joint together with a threaded nut.

In a further embodiment, shown in FIG. 23B, a retaining member 97 such as that shown in FIG. 22, which may be a bolt or the like, can be provided with a bend or curve such that it passes through holes in the articular processes 20, 22, and optionally through an implant 76, if such implant is provided in the facet joint. A nut 94 is threaded onto the distal end of the fastener 97 to secure the articular processes 20, 22 of the facet joint together, as shown in FIG. 23B. Such a curve or bend can be provided in any of the various exemplary retaining member configurations described herein.

Figure 24:
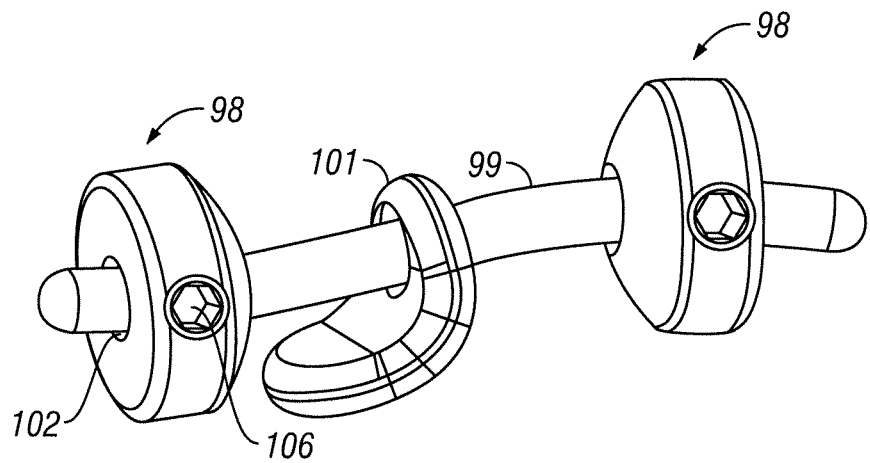
FIG. 24 depicts a retaining member in the shape of a rod or cylinder which is adapted to accept two set-screw retaining rings.
Figure 25A:
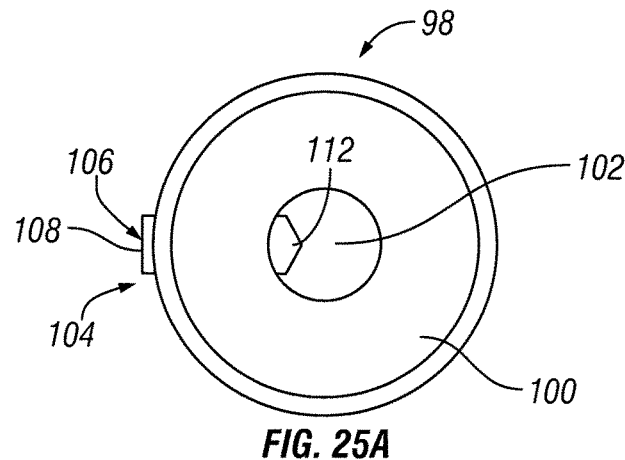
FIGS. 25A and 25B are elevational and cross-sectional views, respectively, of the set-screw retaining rings shown in FIG. 24.
Figure 25B:
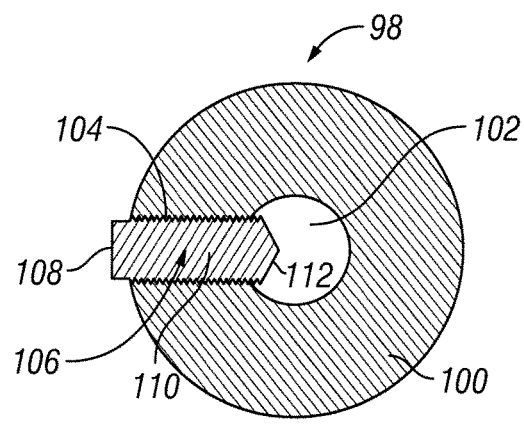

In another embodiment, shown in FIG. 24, the anchoring arrangement includes a retaining member 99 which can be secured to the articular process with retaining rings 98 instead of with threaded nuts. As depicted in FIGS. 25A and 25B, the retaining rings 98 include a ring 100 with a central lumen 102 and a locking element to facilitate locking the ring 100 to the retaining member 99. The central lumen 102 is adapted to accept insertion of the retaining member 99 therethrough. The retaining member 99 also passes through a hole in the implant 101 when placed in the facet joint, similar to the configuration shown in FIG. 21. The illustrated locking element includes a side lumen 104 which is threaded and configured to accept a rotatable screw 106 (e.g., a "set screw") with a proximal end 108, a threaded body 110 and a distal end 112. The threaded body 110 is complementary to the threads of the side lumen 104 so that when the screw 106 is rotated at its proximal end 108, the distal end 112 of the screw 106 moves further into the central lumen 102 and is capable of applying increasing force to the retaining member 99 inserted through the central lumen 102.

Figure 26:
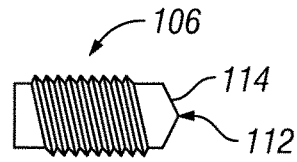
FIGS. 26 through 28 are elevational views of various embodiments of the screw in the set-screw retaining rings.
Figure 27:
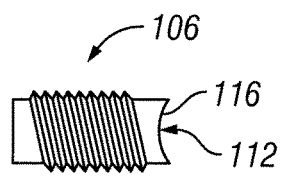
Figure 28:
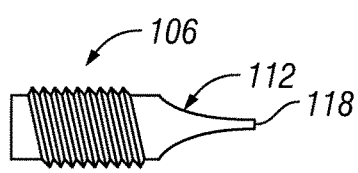

In one embodiment, the force on the retaining member 99 is capable of creating a friction fit or a mechanical fit to resist movement between the retaining member 99 and the retaining ring 98, thereby securing the retaining member 99 to the articular process 20 or 22. As shown in FIGS. 26-28, the distal end 112 of the screw 106 can be configured to engage the retaining member 99 using any of a variety designs, including but no limited to a blunt tip 114, a curved tip 116, or a piercing tip 118.

In another embodiment, depicted in FIGS. 29A and 29B, the retaining member 99 is securable to the articular process 20 or 22 with a retaining disc 120 have radially inward biased projections 122 defining a central lumen 124. The central lumen has a cross-sectional diameter that is smaller than that of the retaining member 99 but is capable of enlargement when the inward projections 122 are bent away, as shown in FIGS. 30A and 30B. The inward projections 122 apply increasing force to the retaining member 99 within the central lumen 124 as the projections 122 are bent, thereby creating a friction fit. The outer perimeter of the retaining disc 120 can have a shape that is non-circular. For example, the shape of the retaining disc 120 can be oval or ovoid, rectangular, polygonal, or any other shape surrounding a central lumen.

In still further embodiments, the retaining member is configured to accept a retaining ring 98 or a retaining disc 120 at or near one end, and has a single threaded end 96 at the opposite end. The retaining member can be inserted through holes in the implant and articular processes 20, 22, and the retaining ring 98 or retaining disc 120 can be fastened at or near the one end of the retaining member as described herein. A single nut 94 can then be threaded onto the threaded end 96 to immobilize the facet joint and more easily provide a compressive force across the joint.

Figure 31:
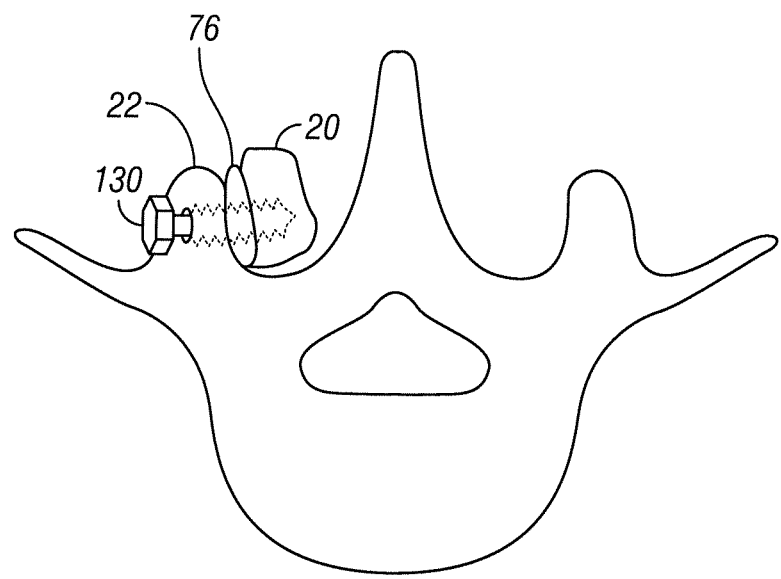
FIG. 31 depicts a retaining member which is a bone screw that is used to affix the implant to the articular processes of a facet joint.

In a still further embodiment, shown in FIG. 31, the retaining member is a bone screw 130 or the like. The bone screw 130 is placed from the medial side of the facet joint to the lateral side thereof, such that it passes through the articular processes 20, 22, and through an implant 76 provided in the facet joint. A small pilot hole can be formed in the articular processes 20, 22 and/or in the implant 76 prior to the insertion of the bone screw 130. Alternatively, the bone screw 130 can be screwed directly through the bone and the implant 76.

In a further aspect, embodiments of the invention provide a method for immobilizing a facet joint. First, a midline skin incision is made over the desired vertebrae, or a paraspinous skin incision is made over the particular facet joint to be immobilized. The facet joint capsule is incised and at least a portion of the cartilage is removed from the joint space between the facets. Preferably, substantially all of the cartilage is removed from the joint space to expose all or a substantial portion of the articular surfaces of the facets. One or both of the adjacent articular surfaces can be roughened to improve contact with an implant and reduce slippage between the implant faces and the articular surfaces of the facets. Such roughening may also promote osteoincorporation of the implant with the articular surfaces.

An implant is provided as described herein that is configured to be positioned within the facet joint. Preferably, at least a portion of each face of the implant is porous and/or roughened. The implant 56 is then inserted into the facet joint 28 between the articular surfaces 20, 22 as shown in FIG. 17. The implant 56 is preferably shaped such that it fits substantially within the facet joint 28 and conforms to the shape of the facet surfaces.

In one embodiment, the implant is bonded to at least a portion of the articular surfaces using an adhesive or sealant, such as a cyanoacrylate, polymethylmethacrylate, or another biocompatible adhesive. Preferably, the thickness of the implant is slightly larger than the natural distance between the opposing articular surfaces. A thicker implant can provide some compressive force between the implant and the articular surfaces, which can help to maintain the implant in a desired position and result in a more secure bond.

In further embodiments, a hole is then formed through the articular surfaces 20, 22 as shown in FIG. 21. A hole can also be formed in the implant 76 at this time, or the implant 76 may be provided with a hole therethrough before it is inserted into the facet joint. A drill, a punch, or any other conventional apparatus or technique can be used to form the holes.

An anchoring arrangement is then used to secure the implant in a fixed position relative to the adjacent facets. The anchoring arrangement can also provide a compressive force between the implant and the facets to promote adhesion and/or osteoincorporation of the implant with the articular surfaces of the facets. Any appropriate anchoring arrangement, such as those described herein, may be used. The surgical site is then closed, cleaned and dressed.

The foregoing merely illustrates the principles of the invention. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention. All patents, patent applications, and other publications cited herein are incorporated herein by reference in their entireties.

What is claimed is:

1. A method of treating vertebral dysfunction, the method comprising:
    opening a facet joint capsule between a first facet and a second facet associated with adjacent vertebral bodies;
    removing at least a portion of cartilage between the two facets;
    roughening at least a portion of articular surfaces of the first and second facets; and
    securing an implant between the two facets to inhibit motion of the first facet with respect to the second facet, wherein an entire periphery of the implant has a thickness that is greater than a thickness measured from a first face to a second face of a central region of the implant.

2. The method of claim 1, wherein the implant is secured using an anchoring assembly.

3. The method of claim 2, wherein the anchoring assembly is configured to provide a compressive force between the implant and each of the adjacent facets of the facet joint.

4. The method of claim 2, wherein the anchoring assembly comprises a rigid fastener.

5. The method of claim 4, wherein the anchoring assembly further comprises at least one retaining disc configured to be secured to the rigid fastener by friction.

6. The method of claim 2, wherein the anchoring assembly comprises a threaded retainer.

7. The method of claim 2, wherein the anchoring assembly comprises at least one of a bolt or a screw.

8. The method of claim 2, wherein the implant comprises an anchoring hole therethrough, and wherein the step of securing the implant comprises:
    drilling a first hole through the first facet and a second hole through the second facet;
    inserting at least a portion of the anchoring assembly through each of the first hole, the second hole, and the anchoring hole; and
    affixing a retainer assembly to at least one end of the anchoring assembly to prevent removal of the anchoring assembly from the holes.

9. The method of claim 8, wherein the step of securing the implant further comprises the step of drilling the anchoring hole through the implant.

10. The method of claim 2, wherein the anchoring assembly is curved along a primary axis thereof.

11. The method of claim 1, wherein the securing step comprises providing a compressive force between the implant and each of the first and second facets.

12. A method of treating a facet joint having a first facet and a second facet, the method comprising:
    drilling a first hole through the first facet;
    opening a joint capsule between the first facet and the second facet;
    inserting an implant in the joint capsule, the implant comprising a first face, a second face, and an aperture extending from the first face to the second face, wherein the first face is positioned apposed a first articular surface of the first facet and the second face is positioned apposed a second articular surface of the second facet, and wherein an entire periphery of the implant has a thickness that is greater than a thickness measured from the first face to the second face of a central region of the implant; and
    inserting at least a portion of an anchoring assembly through the first hole and the aperture of the implant to inhibit motion of the first face with respect to the first articular surface.

13. The method of claim 12, further comprising drilling a second hole through the second facet and inserting at least a portion of the anchoring assembly through the second hole to inhibit motion of the second face with respect to the second articular surface.

14. The method of claim 12, wherein the anchoring assembly comprises at least one enlarged structure adapted to abut a non-articular surface of the first or second facet for providing a compressive force between the implant and the facets.

15. The method of claim 12, wherein the anchoring assembly comprises a rigid fastener.

16. The method of claim 15, wherein the anchoring assembly further comprises at least one retaining disc configured to be secured to the rigid fastener by friction.

17. The method of claim 12, wherein the anchoring assembly comprises a threaded retainer.

18. The method of claim 12, wherein the anchoring assembly comprises at least one of a bolt or a screw.

19. The method of claim 12, wherein the anchoring assembly is curved along a primary axis thereof.

* * * * *